US010458912B2

(12) United States Patent
Chouaib et al.

(10) Patent No.: US 10,458,912 B2
(45) Date of Patent: Oct. 29, 2019

(54) MODEL BASED OPTICAL MEASUREMENTS OF SEMICONDUCTOR STRUCTURES WITH ANISOTROPIC DIELECTRIC PERMITTIVITY

(71) Applicant: KLA-Tencor Corporation, Milpitas, CA (US)

(72) Inventors: Houssam Chouaib, Milpitas, CA (US); Qiang Zhao, Milpitas, CA (US); Andrei V. Shchegrov, Campbell, CA (US); Zhengquan Tan, Cupertino, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/649,843

(22) Filed: Jul. 14, 2017

(65) Prior Publication Data
US 2018/0059019 A1 Mar. 1, 2018

Related U.S. Application Data

(60) Provisional application No. 62/381,987, filed on Aug. 31, 2016.

(51) Int. Cl.
*G01B 11/30* (2006.01)
*G01N 21/47* (2006.01)
(Continued)

(52) U.S. Cl.
CPC ......... *G01N 21/4788* (2013.01); *G01B 11/24* (2013.01); *G01B 11/30* (2013.01);
(Continued)

(58) Field of Classification Search
CPC . G01N 21/4788; G01N 21/9515; G01B 11/30
(Continued)

(56) References Cited

U.S. PATENT DOCUMENTS 5,608,526 A 3/1997 Piwonka-Corle et al.
5,859,424 A 1/1999 Norton et al.
(Continued)

FOREIGN PATENT DOCUMENTS

EP 0720216 A2 7/1996

OTHER PUBLICATIONS

Chouaib, H. and Zhou, Q., "Nanoscale optical critical dimension measurement of a contact hole using deep ultraviolet spectroscopic ellipsometry," J. Vac. Sci. Technol. B 31(1), 011803-1, Jan./Feb. 2013.
(Continued)

*Primary Examiner* — Isiaka O Akanbi
(74) *Attorney, Agent, or Firm* — Spano Law Group; Joseph S. Spano

(57) ABSTRACT

Methods and systems for performing optical, model based measurements of a small sized semiconductor structure employing an anisotropic characterization of the optical dispersion properties of one or more materials comprising the structure under measurement are presented herein. This reduces correlations among geometric parameters and results in improved measurement sensitivity, improved measurement accuracy, and enhanced measurement contrast among multiple materials under measurement. In a further aspect, an element of a multidimensional tensor describing the dielectric permittivity of the materials comprising the structure is modelled differently from another element. In a further aspect, model based measurements are performed based on measurement data collected from two or more measurement subsystems combined with an anisotropic characterization of the optical dispersion of the materials under measurement. In another aspect, the characterization of the optical dispersion of one or more materials compris-
(Continued)

ing the structure under measurement depends on the geometry of the structure.

27 Claims, 11 Drawing Sheets

(51) Int. Cl.
| | | |
|---|---|---|
| *G01N 21/95* | (2006.01) | |
| *G01B 11/24* | (2006.01) | |
| *G03F 7/20* | (2006.01) | |
| *G01N 21/21* | (2006.01) | |
| *G01N 21/956* | (2006.01) | |
| *G01N 21/88* | (2006.01) | |

(52) U.S. Cl.
CPC ....... *G01B 11/303* (2013.01); *G01N 21/9515* (2013.01); *G03F 7/70616* (2013.01); *G03F 7/70625* (2013.01); *G01B 2210/56* (2013.01); *G01N 21/211* (2013.01); *G01N 21/9501* (2013.01); *G01N 21/956* (2013.01); *G01N 2021/8883* (2013.01)

(58) Field of Classification Search
USPC .......................... 356/235.2–237.6, 625, 369
See application file for complete search history.

(56) References Cited

U.S. PATENT DOCUMENTS

| | | | |
|---|---|---|---|
| 5,943,122 A | 8/1999 | Holmes | |
| 5,969,273 A | 10/1999 | Archie | |
| 6,429,943 B1 | 8/2002 | Opsal et al. | |
| 6,633,831 B2 | 10/2003 | Nikoonahad et al. | |
| 6,734,967 B1 | 5/2004 | Piwonka-Corle et al. | |
| 6,816,570 B2 | 10/2004 | Janik et al. | |
| 6,895,075 B2 | 5/2005 | Yokhin et al. | |
| 6,972,852 B2 | 12/2005 | Opsal et al. | |
| 7,414,721 B1* | 8/2008 | Suvkhanov | G01B 11/0641 257/E21.53 |
| 7,478,019 B2 | 1/2009 | Zangooie et al. | |
| 7,515,253 B2* | 4/2009 | Bareket | G01N 21/211 356/369 |
| 7,755,764 B2 | 7/2010 | Kwak et al. | |
| 7,826,071 B2 | 11/2010 | Shchegrov et al. | |
| 7,907,264 B1 | 3/2011 | Krishnan | |
| 7,929,667 B1 | 4/2011 | Zhuang et al. | |
| 7,933,026 B2 | 4/2011 | Opsal et al. | |
| 8,798,966 B1 | 8/2014 | Hench | |
| 8,860,937 B1 | 10/2014 | Dziura et al. | |
| 2009/0033931 A1* | 2/2009 | Murtagh | G01N 21/1717 356/317 |
| 2010/0068834 A1* | 3/2010 | Hachigo | G01N 21/211 438/16 |
| 2012/0226644 A1 | 9/2012 | Jin et al. | |
| 2013/0083320 A1* | 4/2013 | Gao | G01N 21/9501 356/237.5 |
| 2013/0114085 A1 | 5/2013 | Wang et al. | |
| 2014/0019097 A1* | 1/2014 | Bakeman | G06F 17/5068 703/1 |
| 2014/0111791 A1 | 4/2014 | Manassen et al. | |
| 2014/0172394 A1 | 6/2014 | Kuznetsov et al. | |
| 2014/0222380 A1 | 8/2014 | Kuznetsov et al. | |
| 2014/0297211 A1 | 10/2014 | Pandev et al. | |
| 2014/0316730 A1 | 10/2014 | Shchegrov et al. | |
| 2015/0042984 A1 | 2/2015 | Pandev et al. | |
| 2015/0046118 A1 | 2/2015 | Pandev et al. | |
| 2016/0157828 A1* | 6/2016 | Sumi | G01N 29/0654 702/189 |
| 2016/0161245 A1* | 6/2016 | Fu | G01B 11/24 250/208.2 |

OTHER PUBLICATIONS

Mihardja, L. et al., "Data feed-forward for improved optical CD and film metrology," Metrology, Inspection, and Process Control for Microlithography XXVI, Proc. SPIE 8324, 83241H (Mar. 29, 2012).

Tzai, Wei-Jhe et al., "Apply multiple target for advanced gate ADI critical dimension measurement by scatterometry technology," Metrology, Inspection, and Process Control for Microlithography XXVI, Proc. SPIE 8324, 832420 (Mar. 29, 2012).

International Search Report dated Dec. 4, 2017, for PCT Application No. PCT/US2017/047159 filed on Aug. 16, 2017 by KLA-Tencor Corporation, 3 pages.

* cited by examiner

MODEL BASED OPTICAL MEASUREMENTS OF SEMICONDUCTOR STRUCTURES WITH ANISOTROPIC DIELECTRIC PERMITTIVITY

CROSS REFERENCE TO RELATED APPLICATION

The present application for patent claims priority under 35 U.S.C. § 119 from U.S. provisional patent application Ser. No. 62/381,987 entitled "Method of Optical Measurements of Critical Dimensions, Film Thickness and Bandgap of Semiconductor Structures," filed Aug. 31, 2016, the subject matter of which is incorporated herein by reference.

TECHNICAL FIELD

The described embodiments relate to systems for optical characterization of structures and materials employed in semiconductor manufacturing.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

The geometry of structures fabricated on a semiconductor wafer depends on process conditions during lithographic exposure. Process parameters such as focus, dose, and scanner aberration affect the shape of the resulting structures differently, depending on the type of structure being fabricated. For example, relatively isolated structures are more sensitive to focus changes, while relatively dense structures are more sensitive to changes in dosage. Device functionality and manufacturing yield is limited by the quality of the structures formed by patterning steps, e.g., lithography, deposition, etch, etc.

The lateral dimensions of integrated circuit features (e.g., CD) are primarily limited to the resolution of the lithography tools involved in the fabrication process flow. Lithography and etch processes are continuously progressing toward smaller dimensions. Multiple patterning techniques are commonly employed to decrease lateral dimensions of integrated circuits. Today, advanced lithography tools operating at wavelengths of 193i nanometers employ multiple patterning techniques (e.g., double and triple patterning) to realize features having lateral dimensions of less than 20 nanometers. Lateral dimensions are expected to shrink further in upcoming fabrication technology nodes.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry, ellipsometry, and reflectometry implementations and associated analysis algorithms are commonly used to characterize critical dimensions, film thicknesses, bandgap, composition, overlay and other parameters of nanoscale structures.

Existing model based metrology methods typically include a series of steps to model and then measure structure parameters. Typically, measurement data is collected (e.g., DOE spectra) from a particular metrology target. An accurate model of the optical system, dispersion parameters, and geometric features is formulated. Film spectra measurements are collected to determine material dispersions. A parametric geometric model of the target structure is created along with an optical model. In addition, simulation approximations (e.g., slabbing, Rigorous Coupled Wave Analysis (RCWA), etc.) must be carefully performed to avoid introducing excessively large errors. Discretization and RCWA parameters are defined. A series of simulations, analysis, and regressions are performed to refine the geometric model and determine which model parameters to float. A library of synthetic spectra is generated. Finally, measurements are performed using the library and the geometric model.

Optical metrology processes are used at various steps during a semiconductor manufacturing process to detect defects on wafers to promote higher yield and optimize device performance. As design rules and process windows continue to shrink in size, characterization becomes more difficult. In addition, the increasing number of parameters required to characterize complex structures, leads to increasing parameter correlation. As a result, the parameters characterizing the target often cannot be reliably decoupled with available measurements.

Existing methods assume that the materials comprising a semiconductor structure under measurement are optically isotropic (i.e., material parameters are the same regardless of the azimuth angle, angle of incidence, electric field polarization, etc.). For small feature sizes, this results in significant subsystem mismatch, even for simple optical critical dimension (OCD) structures, poor spectral fit quality especially among combinations of different measurement settings, inaccurate geometric profiles, large disagreement with reference measurements (e.g., transmission electron microscopy (TEM), CD scanning electron microscopy (CDSEM), etc.), and lower medium contrast, and as a result, higher correlation among geometric parameters. These issues are described in greater detail in the article entitled, "Nanoscale optical critical dimension measurement of a contact hole using deep ultraviolet spectroscopic ellipsometry", by H. Chouaib and Q. Zhou, published in J. Vac. Sci. Technol. B 31, 011803 (2013), the subject matter of which is incorporated herein by reference in its entirety.

In response to these challenges, more complex optical metrology tools have been developed. For example, tools with multiple angles of illumination, shorter illumination wavelengths, broader ranges of illumination wavelengths, and more complete information acquisition from reflected signals (e.g., measuring multiple Mueller matrix elements in addition to the more conventional reflectivity or ellipsometric signals) have been developed.

However, these approaches have not reliably overcome fundamental challenges associated with measurement of many advanced targets (e.g., complex 3D structures, structures smaller than 10 nm, structures employing opaque materials) and measurement applications (e.g., line edge roughness and line width roughness measurements).

Accordingly, it would be advantageous to develop high throughput systems and methods for characterizing structures and materials in the semiconductor manufacturing process. In particular, it would be advantageous to develop a robust, reliable, and stable approach to in-line metrology of semiconductor structures having small feature size (e.g., less than 20 nanometers).

SUMMARY

Methods and systems for performing optical, model based measurements of a small sized semiconductor structure (e.g., CD structures, overlay structures, thin films, etc.) employing an anisotropic characterization of the optical dispersion properties of one or more materials comprising the structure under measurement are presented herein. This reduces correlations among geometric parameters and results in improved measurement sensitivity, improved measurement accuracy, and enhanced measurement contrast among multiple materials under measurement.

In some embodiments, the structure under measurement includes two or more geometric features each fabricated from a different material. In some of these embodiments, a structural model includes an anisotropic characterization of the optical dispersion properties of one or more of these different materials.

In a further aspect, model based measurements are performed based on measurement data collected from two or more measurement subsystems combined with an anisotropic characterization of the optical dispersion of the materials under measurement.

In another aspect, model based measurements are performed at azimuth angles selected to align with the principle axes of the geometry under measurement. This assumption may be advantageous when performing measurements of stacked structures having features patterned with periodicity in one direction. In these embodiments, the material characterization of a structure under measurement is varied depending on the azimuth angle associated with each measurement.

In another further aspect, an initial estimate of values of one or more parameters of interest is determined based on optical measurements performed at a single orientation of the incident illumination beam with respect to the measurement target. The initial, estimated values are implemented as the starting values of the parameters of interest for a regression of the measurement model with measurement data collected from optical measurements at multiple orientations. In this manner, a close estimate of a parameter of interest is determined with a relatively small amount of computational effort, and by implementing this close estimate as the starting point for a regression over a much larger data set, a refined estimate of the parameter of interest is obtained with less overall computational effort.

In one example, the initial values of the optical dispersion parameters of each measurement channel (i.e., subsystem) are seeded with bulk parameter values or dispersion parameter values determined from a film target of the same material under measurement.

In another aspect, model based measurements are performed with the assumption that off-diagonal elements of the dielectric permittivity matrix are assumed to be zero valued. This simplifies electromagnetic model building and fitting analysis significantly.

In another aspect, optical model based measurements of semiconductor structures incorporate a characterization of the optical dispersion of one or more materials comprising the structure under measurement that depends on the geometry of the structure.

In a further aspect, the optical dispersion parameters are varied during regression as the estimated values of the underlying geometric parameters are iteratively updated. In one example, the floating material parameters are used to monitor the structural parameters of interest using an optical response model that characterizes a quantum effect. In this sense, the estimation of material parameter values characterized in part by geometric parameters enhances measurement sensitivity to the geometric parameters.

In a further aspect, one or more of the elements of the multidimensional tensor describing the dielectric permittivity are modelled differently. For example, different multi-oscillator models may be used for different elements of the multidimensional tensor, $\varepsilon_{ij}(\lambda,g)$. The oscillator constants associated with each different model of the model depend on the structure geometry.

In some embodiments, a geometric parameter of interest is estimated based on a difference between the dispersion parameter values estimated based on an isotropic model and the same dispersion parameter values estimated based on an anisotropic model of optical dispersion.

In a further aspect, a measurement recipe associated with a particular measurement application is optimized for highest sensitivity and lowest correlation among floating parameters of the anisotropic model of optical dispersion.

In another further aspect, device performance is improved by controlling a process of manufacture of the semiconductor wafer based at least in part on the estimated parameters of interest.

In another further aspect, separate estimates of parameters of interest associated with different features of a structure under measurement are made based on the same spectral response data. For example, a wafer under measurement may include multiple layers and structural features. The measured spectral response data includes contributions from all of these layers and features. A measurement model that captures the contributions of each of these layers and features can be used to separately determine parameters of interest associated with each different physical layer or feature under analysis.

The foregoing is a summary and thus contains, by necessity, simplifications, generalizations, and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Figure 1:
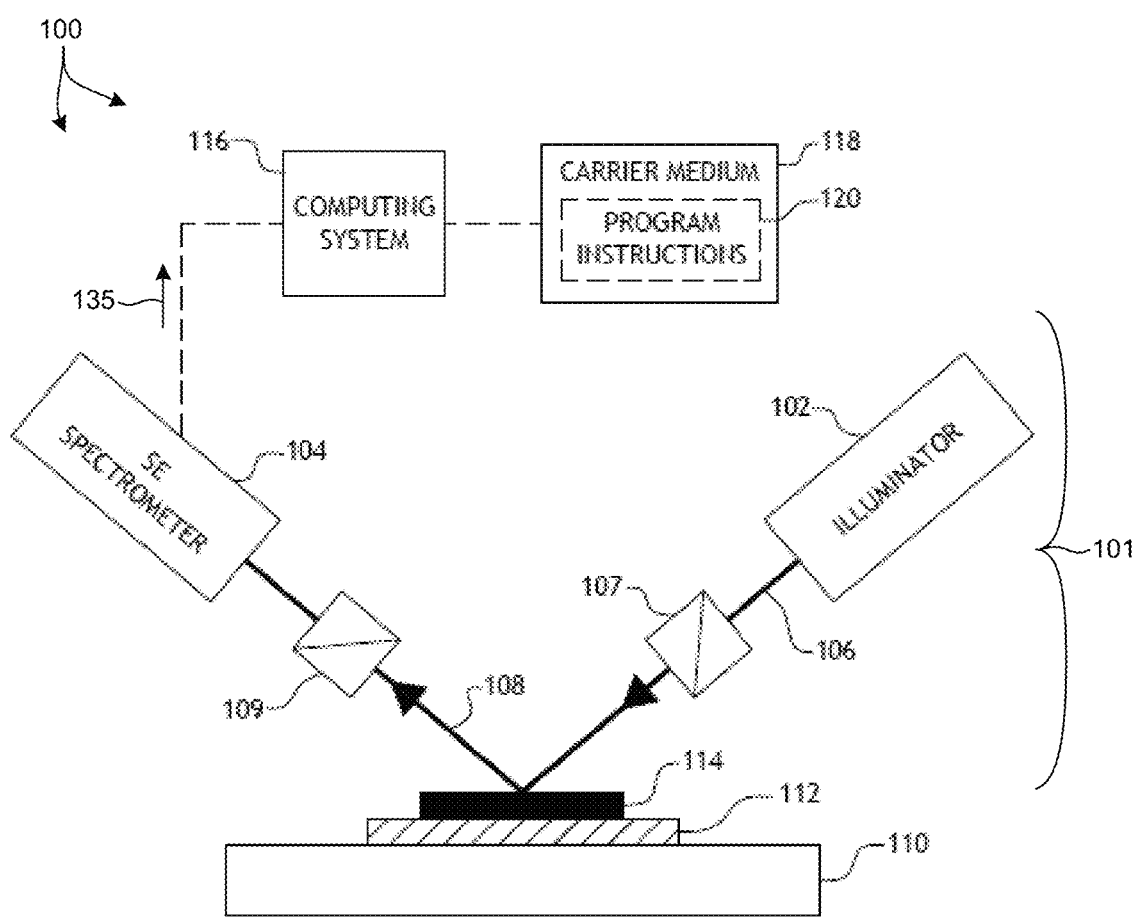
FIG. 1 is a simplified diagram illustrative of a system 100 for measuring a spectral response of a structure fabricated on a semiconductor wafer, in accordance with at least one embodiment of the present invention.

Reference will now be made in detail to background examples and some embodiments of the invention, examples of which are illustrated in the accompanying drawings.

Methods and systems for performing optical, model based measurements of a small sized semiconductor structure (e.g., CD structures, overlay structures, thin films, etc.) employing an anisotropic characterization of the optical dispersion properties of one or more materials comprising the structure under measurement are presented herein. This reduces correlations among geometric parameters and results in improved measurement sensitivity, improved measurement accuracy, and enhanced measurement contrast among multiple materials under measurement.

In some embodiments, optical model based measurements of semiconductor structures incorporate an anisotropic characterization of the dielectric permittivity or the complex index of refraction of one or more materials comprising the structure under measurement.

In general, the electric displacement field, D, is related to the incident electric field, E, by the dielectric permittivity, $\varepsilon$, as described in equation (1), where $\varepsilon_0$ is the vacuum permittivity.

$$D = \varepsilon_0 \varepsilon E \quad (1)$$

Traditionally, materials comprising semiconductor structures under measurement are treated as isotropic (i.e., the response of the material to incident light is the same regardless of direction). Hence, the dielectric permittivity is treated as a scalar function $\varepsilon(\lambda)$. However, to account for the dependence of the dielectric function on direction, the dielectric function is treated as a multidimensional tensor. In some embodiments, the dielectric function is treated as a matrix, $\varepsilon_{ij}(\lambda)$. For example, in a three dimensional space characterized by three principle, orthogonal directions, x, y, and z, the x, y, and z components of the D-field are related to the x, y, and z components of the E-field through the dielectric permittivity matrix, $\varepsilon_{ij}(\lambda)$, as described in equation (2).

$$\varepsilon_{ij}(\lambda) = \begin{pmatrix} \varepsilon_{xx} & \varepsilon_{xy} & \varepsilon_{xz} \\ \varepsilon_{yx} & \varepsilon_{yy} & \varepsilon_{yz} \\ \varepsilon_{zx} & \varepsilon_{zy} & \varepsilon_{zz} \end{pmatrix} \quad (2)$$

In this embodiment, the anisotropic characterization of the optical dispersion includes an optical dispersion parameter, $\varepsilon_{ij}$, associated with each of three principle directions, and the value of the optical dispersion parameter associated with at least one of the three principle directions is different from the others. In one example, the value of $\varepsilon_{zz}$ is different from the values of $\varepsilon_{xx}$ and $\varepsilon_{yy}$. The complex refractive indices, n and k, are related to the dielectric permittivity by equation (3).

$$n(\lambda) + ik(\lambda) = \sqrt{\varepsilon(\lambda)} \quad (3)$$

In this manner, each element of the permittivity matrix can be expressed in terms of dispersion parameters, n and k, and vice-versa.

In general, an anisotropic optical dispersion model as described herein may be characterized any useful optical dispersion metric. For example, an anisotropic optical dispersion model may be characterized by the real (n) and imaginary (k) components of the complex index of refraction. In another example, an anisotropic optical dispersion model may be characterized by the real ($\varepsilon_1$) and imaginary ($\varepsilon_2$) components of the complex dielectric permittivity. In other examples, the anisotropic optical dispersion model may be characterized by any of the square root of $\varepsilon_2$, absorption constant $\alpha = 4\pi k/\lambda$, conductivity ($\sigma$), skin depth ($\delta$), and attenuation constant $(\sigma/2)*\text{sqrt}(\mu/\varepsilon)$, where $\mu$ is the free space permeability, etc. In other examples, the optical dispersion model may be described by any combination of the aforementioned optical dispersion metrics. The aforementioned optical dispersion metrics are provided by way of non-limiting example. Other optical dispersion metrics or combinations of metrics may be contemplated.

FIG. 1 illustrates a system 100 for measuring a spectral response of a structure fabricated on a semiconductor wafer, in accordance with at least one embodiment of the present invention. As shown in FIG. 1, the system 100 may be used to perform spectroscopic ellipsometry on one or more structures 114 of a semiconductor wafer 112 disposed on a translation stage 110. In this aspect, the system 100 may include a spectroscopic ellipsometer equipped with an illuminator 102 and a spectrometer 104. The illuminator 102 of the system 100 is configured to generate and direct illumination of a selected wavelength range (e.g., 150-2500 nm) to the structure 114 disposed on the surface of the semiconductor wafer 112. In turn, the spectrometer 104 is configured to receive light from the surface of the semiconductor wafer 112 in response to the illumination delivered to structure 114. It is further noted that the light emerging from the illuminator 102 is polarized using polarizer 107 to produce a polarized illumination beam 106. The radiation reflected by the structure 114 disposed on the wafer 112 is passed through an analyzer 109 and to the spectrometer 104. In this regard, the radiation received by the spectrometer 104 in the collection beam 108 is compared to the incident radiation of the illumination beam 106, allowing for spectral analysis of structure 114.

In a further embodiment, the system 100 may include one or more computing systems 116. The one or more computing systems 116 may be communicatively coupled to the spectrometer 104. In one aspect, the one or more computing systems 116 may be configured to receive a set of spectral measurements performed by the spectrometer 104 on one or more wafers. Upon receiving results of the one or more sampling process from the spectrometer, the one or more computing systems 116 may then calculate values of structural parameters associated with a measurement model representative of the spectroscopic measurement of structure 114. In one example, the computing system 116 may extract a value of a critical dimension (CD) of a feature of structure 114 based on a regression of the measurement model with the acquired spectrum from the spectrometer 104.

In another further embodiment, the computing system 116 may control a process of manufacture of a semiconductor wafer based at least in part on the determined values of one or more structural parameters. For example, computing system 116 may be configured to communicate process control parameter values to one or more manufacturing tools (e.g., lithography tool, etch tool, etc.) responsible for the manufacture of the semiconductor wafers being measured.

It should be recognized that the various steps described throughout the present disclosure may be carried out by a single computer system 116 or, alternatively, a multiple computer system 116. Moreover, different subsystems of the system 100, such as the spectroscopic ellipsometer 101, may include a computer system suitable for carrying out at least a portion of the steps described above. Therefore, the above description should not be interpreted as a limitation on the present invention but merely an illustration. Further, the one or more computing systems 116 may be configured to perform any other step(s) of any of the method embodiments described herein.

In another embodiment, the computer system 116 may be communicatively coupled to the spectrometer 104 or the illuminator subsystem 102 of the ellipsometer 101 in any manner known in the art. For example, the one or more computing systems 116 may be coupled to a computing system of the spectrometer 104 of the ellipsometer 101 and a computing system of the illuminator subsystem 102. In another example, the spectrometer 104 and the illuminator 102 may be controlled by a single computer system. In this manner, the computer system 116 of the system 100 may be coupled to a single ellipsometer computer system.

The computer system 116 of the system 100 may be configured to receive and/or acquire data or information from the subsystems of the system (e.g., spectrometer 104, illuminator 102, and the like) by a transmission medium that may include wireline and/or wireless portions. In this manner, the transmission medium may serve as a data link between the computer system 116 and other subsystems of the system 100. Further, the computing system 116 may be configured to receive spectral results via a storage medium (i.e., memory). For instance, the spectral results obtained using a spectrometer of an ellipsometer may be stored in a permanent or semi-permanent memory device. In this regard, the spectral results may be imported from an external system.

Moreover, the computer system 116 may send data to external systems via a transmission medium. Moreover, the computer system 116 of the system 100 may be configured to receive and/or acquire data or information from other systems (e.g., inspection results from an inspection system or metrology results from a metrology system) by a transmission medium that may include wireline and/or wireless portions. In this manner, the transmission medium may serve as a data link between the computer system 116 and other subsystems of the system 100. Moreover, the computer system 116 may send data to external systems via a transmission medium.

The computing system 116 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 120 implementing methods such as those described herein may be transmitted over or stored on carrier medium 118. The carrier medium may be a transmission medium such as a wire, cable, or wireless transmission link. The carrier medium may also include a computer-readable medium such as a read-only memory, a random access memory, a magnetic or optical disk, or a magnetic tape.

The embodiments of the system 100 illustrated in FIG. 1 may be further configured as described herein. In addition, the system 100 may be configured to perform any other step(s) of any of the method embodiment(s) described herein.

Figure 2:
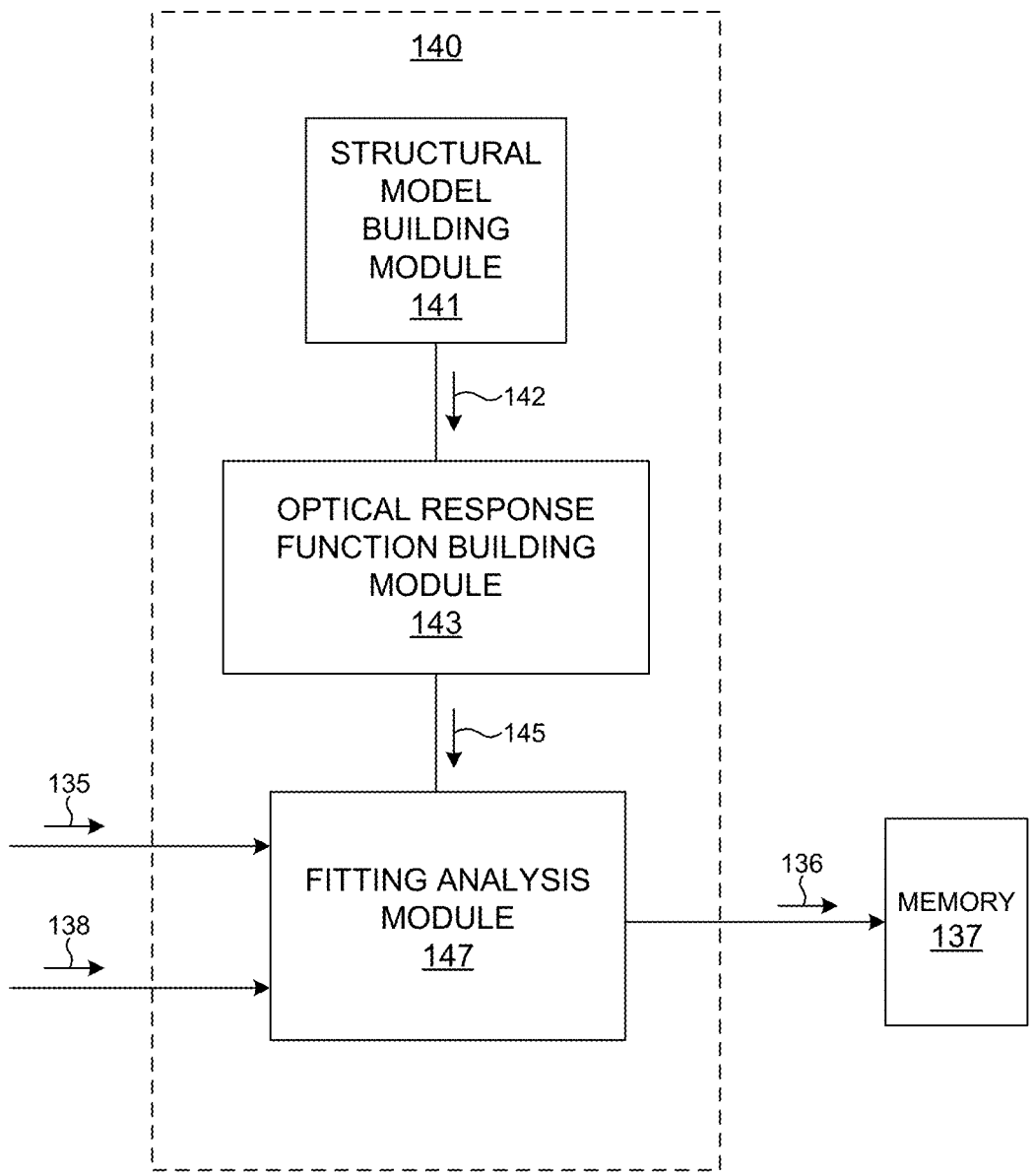
FIG. 2 is a diagram illustrative of an exemplary model building and analysis engine 140 implemented by computing system 116 of system 100 depicted in FIG. 1.

FIG. 2 is a diagram illustrative of an exemplary model building and analysis engine 140 implemented by computing system 116. As depicted in FIG. 2, model building and analysis engine 140 includes a structural model building module 141 that generates a structural model 142 of a measured structure of a specimen under measurement. In some embodiments, structural model building module 141 also incorporates a process model to generate structural model 142.

In one aspect, structural model 142 includes anisotropic material properties of the specimen. In some embodiments, the structure under measurement includes two or more geometric features each fabricated from a different material. In some of these embodiments, the structural model includes an anisotropic characterization of the optical dispersion properties of one or more of these different materials. In some embodiments, the structural model building module 141 is implemented in the AcuShape software product manufactured by KLA-Tencor, Corporation, Milpitas, Calif. (USA). In one example, the AcuShape software includes a set of geometric features (e.g., 1D layer, 2D trapezoid, 3D post, etc.) that are joined together and parameterized to simulate the structure under measurement. In addition, the AcuShape software includes a set of anisotropic building blocks available for the user to assign anisotropic material behavior to any of the modeled structural features. In one example, the AcuShape software provides the user the option to assign different n(λ) and k(λ) values in each principle direction for each geometric feature of the modeled structure under measurement. In this manner, the user is able to select which material (i.e., which portion of the modeled structure) will be characterized with anisotropic dispersion properties.

The structural model 142 is received as input to optical response function building module 143. Optical response function building module 143 generates a measurement model 145 based at least in part on the structural model 142. In one aspect, optical response function building module 143 employs an anisotropic characterization of the optical dispersion properties of the structure under measurement to generate measurement model 145 as described herein.

In some embodiments, optical response function building module 143 characterizes the optical interaction of the incident beam with the structure under measurement using an electro-magnetic solver employing algorithms such as rigorous coupled wave analysis (RCWA), finite element method (FEM), method of moments, surface integral method, volume integral method, finite difference, time domain (FDTD) method, and others. In some embodiments, the optical dispersion models described herein are implemented in the Film Thickness Measurement Library (FTML) of the Off-line Spectral Analysis (OLSA) stand-alone software available from KLA-Tencor Corporation, Milpitas, Calif. (USA).

Measurement model 145 is received as input to fitting analysis module 147. The fitting analysis module 147 compares the modeled optical response with the corresponding measured data 135 to determine geometric as well as material properties of the specimen 136 for a given set of measurement system parameter values 138 (e.g., angle of incidence, azimuth angle, illumination polarization, electric field orientation, etc.). In the embodiment depicted in FIG. 2, the properties 136 determined by computer system 116 are stored in a permanent or semi-permanent memory device (e.g., memory 137).

Fitting analysis module 147 analyzes measured spectral data by any number of different data fitting and optimization techniques. By way of non-limiting example, fitting analysis module 147 may implement library matching techniques, fast-reduced-order modeling techniques, regression, machine-learning algorithms such as neural networks, support-vector machines (SVM), dimensionality-reduction algorithms such as principle component analysis (PCA), independent component analysis (ICA), local-linear embedding (LLE), sparse representation techniques such as Fourier or wavelet transform techniques, Kalman filtering, and algorithms to promote matching across the same or different tool types, etc. The fitting of spectral measurement data is advantageous for any type of optical technology that provides sensitivity to geometric and/or material parameters of interest. Specimen parameters can be deterministic (e.g., CD, SWA, etc.) or statistical (e.g., rms height of sidewall roughness, roughness correlation length, etc.) as long as proper models describing optical beam interaction with the specimen are used.

In some examples, the fitting of modeled data to experimental data is achieved by minimizing a chi-squared value. For example, for optical measurements, a chi-squared value can be defined as $$\chi_{opt}^2 = \frac{1}{N_{opt}} \sum_j^{N_{opt}} \frac{(S_j^{opt-model}(v_1, \ldots, v_L) - S_j^{opt-experiment})^2}{\sigma_{opt,j}^2} \quad (4)$$

Where, $S_j^{opt-experiment}$ is the measured optical signals 135 in the "channel" j, where the index j describes a set of system parameters such as angle of incidence, azimuth angle, illumination polarization, etc. $S_j^{opt-model}(v_1, \ldots, v_L)$ is the modeled optical signal $S_j$ for the "channel" j, evaluated for a set of structure (target) parameters $v_1, \ldots, v_L$, where these parameters describe geometric (CD, sidewall angle, overlay, etc.) and material (index of refraction, etc.) characteristics. $\sigma_{opt,j}$ is the uncertainty associated with the jth channel. $N_{opt}$ is the total number of channels in the optical metrology. L is the number of parameters characterizing the metrology target.

Equation (4) assumes that the uncertainties associated with different channels are uncorrelated. In examples where the uncertainties associated with the different channels are correlated, a covariance between the uncertainties, can be calculated. In these examples a chi-squared value for optical measurements can be expressed as $$\chi_{opt}^2 = \frac{1}{N_{opt}} (\vec{S}_j^{opt-model}(v_1, \ldots, v_M) - \vec{S}_j^{opt-experiment})^T \quad (5)$$
$$V_{opt}^{-1} (\vec{S}_j^{opt-model}(v_1, \ldots, v_M) - \vec{S}_j^{opt-experiment})$$

where, $V_{opt}$ is the covariance matrix of the optical channel uncertainties, and T denotes the transpose.

In some examples, fitting analysis module 147 resolves at least one specimen parameter value by performing a fitting analysis on optical measurement data 135 with the measurement model 145. In some examples, $\chi_{opt}^2$ is optimized. In one example, the parameter values of an optical dispersion model of the real ($\varepsilon_1$) and imaginary ($\varepsilon_2$) components of the dielectric permittivity across the selected spectral range are determined utilizing a regression process. In this regard, a regression analysis may be applied to the measured spectral data using a selected anisotropic dispersion model.

As described hereinbefore, the fitting of optical data is achieved by minimization of chi-squared values. However, in general, the fitting of optical data may be achieved by other functions.

In some examples, model building and analysis engine 140 improves the accuracy of measured parameters by any combination of feed sideways analysis, feed forward analysis, and parallel analysis. Feed sideways analysis refers to taking multiple data sets on different areas of the same specimen and passing common parameters determined from the first dataset onto the second dataset for analysis. Feed forward analysis refers to taking data sets on different specimens and passing common parameters forward to subsequent analyses using a stepwise copy exact parameter feed forward approach. Parallel analysis refers to the parallel or concurrent application of a non-linear fitting methodology to multiple datasets where at least one common parameter is coupled during the fitting.

Multiple tool and structure analysis refers to a feed forward, feed sideways, or parallel analysis based on regression, a look-up table (i.e., "library" matching), or another fitting procedure of multiple datasets. Exemplary methods and systems for multiple tool and structure analysis is described in U.S. Pat. No. 7,478,019, issued on Jan. 13, 2009, to KLA-Tencor Corp., the entirety of which is incorporated herein by reference. Additional discussion of feed forward analysis is described in the article entitled, "Data feed-forward for improved optical CD and film metrology" by L. Mihardja et al., published in Proc. SPIE 8324, Metrology, Inspection, and Process Control for Microlithography XXVI, 83241H (Mar. 29, 2012), the subject matter of which is incorporated herein by reference in its entirety. Additional discussion of parallel analysis is described in the article entitled, "Apply multiple target for advanced gate ADI critical dimension measurement by scatterometry technology" by Wei-Jhe Tzai et al., published in Proc. SPIE 8324, Metrology, Inspection, and Process Control for Microlithography XXVI, 832420 (Mar. 29, 2012), the subject matter of which is incorporated herein by reference in its entirety.

In some embodiments, one or more optical dispersion parameters (e.g., $n(\lambda)$, $k(\lambda)$, etc.) are treated as variables during fitting analysis. In this manner, the dispersion parameters are allowed to change value for a particular measurement depending on the optical electric field directions, light polarization, illumination angle of incidence, and illumination azimuth angle. Thus, the anisotropic material response is effectively captured during spectroscopic measurements of structures having small sized features (e.g., semiconductor structures having feature sizes less than 20 nanometers).

Material dimensions of many new generation semiconductor structures are so small that quantum effects are significantly impacting measurement accuracy, subsystem matching, etc. As feature sizes shrink below the de Broglie wavelength, unexpected optical response behavior is exhibited. In these examples, one or more materials comprising the nanostructures under measurement exhibit an anisotropic optical response to incoming optical illumination at the elemental level. In some examples, the optical dispersion parameters (e.g., the index of refraction, $n(A)$, and the extinction coefficient, $k(A)$) depend on the material dimensions (e.g., thickness, CD, SWA). In some examples, the material dimensions depend on the measurement subsystems employed to perform the measurement.

Traditionally, bulk dispersion parameter values are assumed for measurements of CD structures. However, the inventors have discovered that the dispersion parameter values obtained from bulk measurements of the material under measurement are no longer valid for use in an optical model based measurement of a small sized feature fabricated from the same material. In these examples, semiconductor materials shaped as small sized features interact with measurement light in a different way than a thick bulk layer of the same material. This manifests itself in optical measurements of metals and some thin semiconductors features (e.g., polysilicon, silicon, silicon germanium, silicon carbide, etc.).

Figure 3:
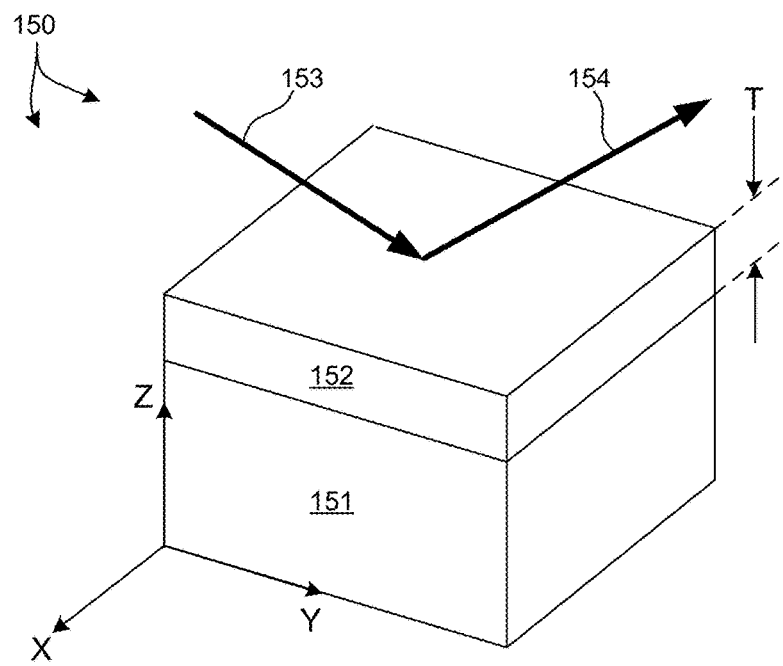
FIG. 3 is a diagram illustrative of an exemplary structure 150 under measurement, for example, by system 100.

FIG. 3 depicts an exemplary structure 150 under measurement, for example, by SE measurement system 100 operating at an angle of incidence of 65 degrees. Structure 150 is a very simple film stack metrology target having a thin layer of Tungsten oriented horizontally (i.e., in the x-y plane) with respect to the substrate 112. In this example, a thin layer of Tungsten 152 having a thickness, T, is fabricated on a layer 151 of different material. Light 154 is collected by spectrometer 104 in response to illumination light 153 provided by illumination source 102.

Figure 4:
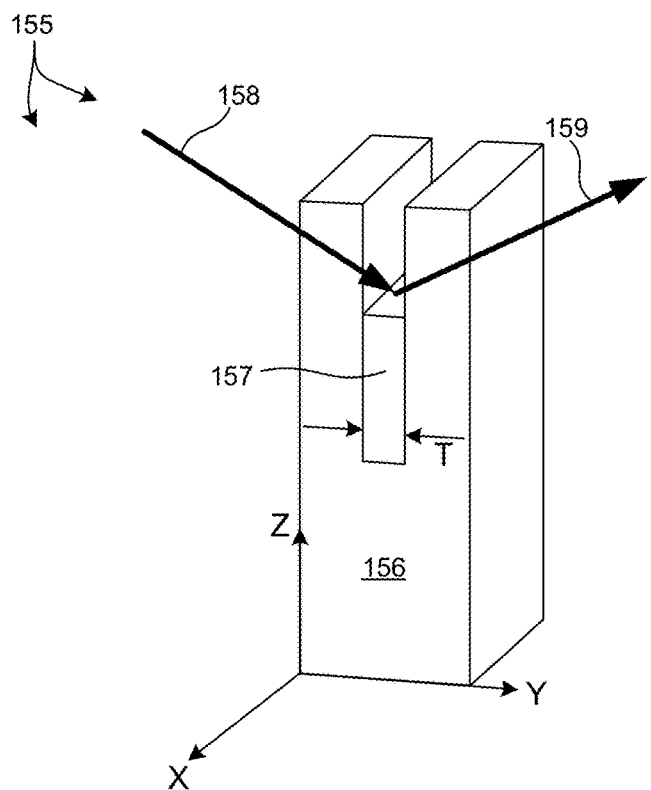
FIG. 4 is a diagram illustrative of another exemplary structure 155 under measurement, for example, by system 100.

FIG. 4 depicts another exemplary structure 155 under measurement, for example, by measurement system 100 operating at an angle of incidence of 65 degrees. Structure 155 is a CD target having a CD structure 157 oriented vertically (i.e., perpendicular to the x-y plane) with respect to the substrate 112. In this example, a Tungsten CD structure 157 having a thickness, T, is fabricated within several layers of a different material structure 156. Light 159 is collected by spectrometer 104 in response to illumination light 158 provided by illumination source 102.

Figure 5:
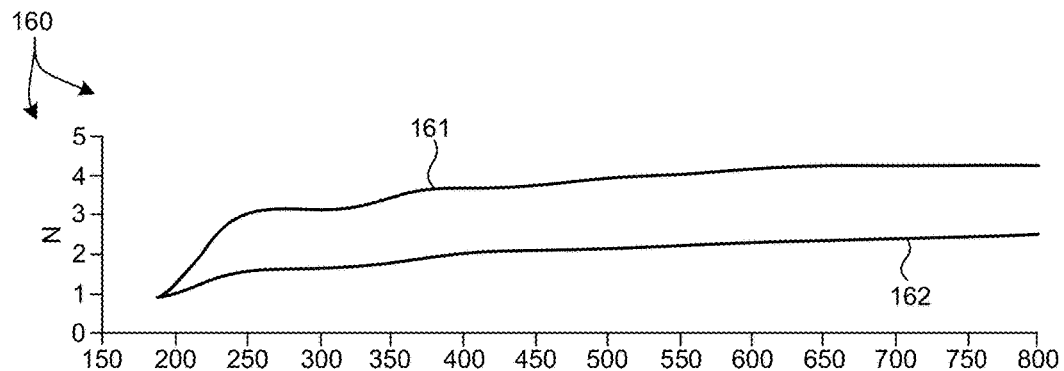
FIG. 5 illustrates a plot 160 of values of the real component, n, of the complex index of refraction measured by measurement system 100 depicted in FIG. 1 over a range of illumination wavelengths.

FIG. 5 depicts a plot 160 of values of the real component, n, of the complex index of refraction measured by measurement system 100 depicted in FIG. 1 over a range of illumination wavelengths. In this example, values of the real and imaginary components of the complex index of refraction are floated in a regression of the measured spectra with a corresponding measurement model associated with the measurement of structure 150. Similarly, the values of the real and imaginary components of the complex index of refraction are floated in a regression of the measured spectra with a corresponding measurement model associated with the measurement of structure 155. Plotline 162 depicts the estimated values of n associated with measurements of structure 150 depicted in FIG. 3. Plotline 161 depicts the estimated values of n associated with measurements of structure 155 depicted in FIG. 4.

Figure 6:
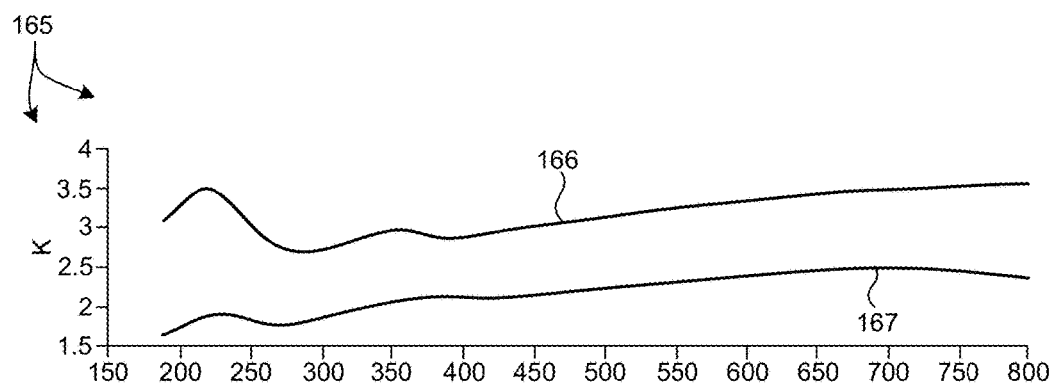
FIG. 6 illustrates a plot 165 of values of the imaginary component, k, of the complex index of refraction measured by measurement system 100 depicted in FIG. 1 over a range of illumination wavelengths.

Similarly, FIG. 6 depicts a plot 165 of values of the imaginary component, k, of the complex index of refraction measured by measurement system 100 depicted in FIG. 1 over a range of illumination wavelengths. Plotline 167 depicts the measured values of k associated with measurements of structure 150 depicted in FIG. 3. Plotline 166 depicts the measured values of k associated with measurements of structure 155 depicted in FIG. 4.

Traditionally, one would expect the measured n and k values to be the same for both structures 150 and 155. However, in this example, the thickness, T, associated with the film and CD structures is ten nanometers, and the measured n and k values are significantly different. This example illustrates that the values of the dispersion parameters (i.e., n and k) are very sensitive to the dimensions of structure under measurement and the orientation of the Tungsten structure relative to surrounding structures. For the CD structure 155, free electrons in the Tungsten nanostructure are affected by surrounding materials at the neighboring interfaces. As a result, the CD structure 155 exhibits anisotropic material response behavior.

The dispersion of the film structure 150 was measured with an excellent spectral fit (i.e., $\chi2 \sim 10$). However, when the same film dispersion model (i.e., same dispersion parameter values) was employed for the measurement of CD structure 155, the spectral fitting was relatively poor (i.e., $\chi2 \sim 15000$). This indicates that the Tungsten film dispersion associated with the film stack structure 150 is not valid for small linewidth structures such as CD structure 155. It also indicates that the optical properties of Tungsten change significantly at a Tungsten linewidth, T, of 10 nanometers.

In this example, a different material dispersion model was developed for CD structure 155 by floating the n and k values. Plotlines 161 and 166 illustrate the results of the measurement fit to the new model. In this example, the spectral fitting was quite good (i.e., $\chi^2 < 100$); a vast improvement over the traditional modelling approach. As illustrated in FIGS. 5 and 6, the extinction coefficient, k, is enhanced when the Tungsten is confined and the refractive index, n, increases as well.

In a further aspect, model based measurements are performed based on measurement data collected from two or more measurement subsystems combined with an anisotropic characterization of the optical dispersion of the materials under measurement. Measurements of nanoscale features performed based on measurement data collected by multiple measurement subsystems are more accurate when the underlying materials are characterized by an anisotropic dielectric function. In these examples, the anisotropic material characterization of a structure under measurement is varied depending on any number of different measurement systems collecting data at any number of different measurement system parameters, or combinations thereof. For purposes of this patent document a measurement subsystem describes a particular measurement system configured to perform measurements at a particular set of measurement system parameters. Thus, a change in measurement system or a change in measurement system parameter values results in a different measurement subsystem. In some examples, the anisotropic material characterization of a structure under measurement is varied among different measurement subsystems by changing any of angle of incidence, illumination polarization, optical electric field orientation, etc.

In general, many model based measurements are performed based on measurement data collected from multiple measurement channels (i.e., subsystems) to optimize parameter sensitivity, increase measurement precision, and minimize correlation to other parameters. One advantage of using SE measurement systems is the wide range of measurement subsystems available. For example, a SE system may include wide ranges of angle of incidence (AOI), analyzer angle (AA), azimuth angle (AZ), and wavelength. In one example, the azimuth angle can have a great impact on measurement sensitivity and precision. Spectroscopic measurement systems such as the SpectraShape™, Shelby™, and Viking™ systems manufactured by KLA-Tencor Corporation, Milpitas, Calif. (USA) offer a diverse array of optical technologies to enable comprehensive and rapid characterization of a wide range of structures.

Traditionally, for challenging metrology targets, high parameter correlation among measurement data collected from different subsystems is a persistent problem. High parameter correlation among different subsystems effectively means that multiple measurement channels do not agree on a value of a parameter of interest associated with a particular measurement model. However, by performing model based measurements based on measurement data collected from two or more measurement subsystems combined with an anisotropic characterization of the optical dispersion of the materials under measurement, parameter correlation is reduced.

In some embodiments, model based measurements are performed based on measurement data collected from two or more azimuth angles combined with an anisotropic characterization of the optical dispersion of the materials under measurement.

Figure 7A:
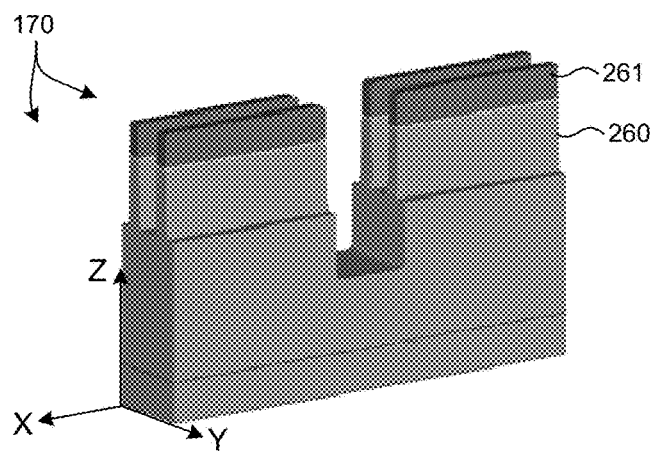
FIGS. 7A-C are diagrams illustrative of different views of an exemplary structure 170 under measurement, for example, by measurement system 100.

FIG. 7A depicts an illustration of an exemplary structure 170 under measurement, for example, by measurement system 100. In this example, structure 170 includes a silicon shallow trench isolation (STI) structure 260 and silicon nitride fin structures 261 fabricated on top of the STI structure 260.

Figure 7B:
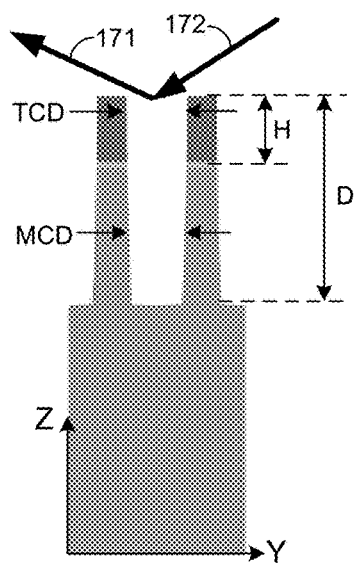
Figure 7C:
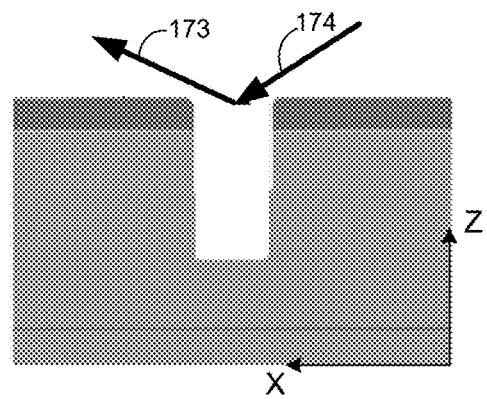

FIG. 7B depicts an illustration of a cross sectional view of structure 170 across the y-z plane depicted in FIGS. 7A-C.

As depicted in FIG. 7B, structure 170 is parameterized by a trench depth, D, a top critical dimension (TCD) of the trench, and a height (H) of the silicon nitride fin structures. In this example, measurement system 100 measures structure 170 at two different azimuth angles (i.e., two different measurement subsystems). FIG. 7B illustrates light 171 collected by spectrometer 104 in response to illumination light 172 provided by illumination source 102 at an orientation that is aligned with the y-z plane depicted in FIGS. 7A-C. At this angle, illumination light 172 is oriented parallel to the direction of periodicity of the fin structures of structure 170 (i.e., parallel to the y-direction).

FIG. 7C depicts an illustration of a cross sectional view of structure 170 across the x-z plane depicted in FIGS. 7A-C. FIG. 7C illustrates light 173 collected by spectrometer 104 in response to illumination light 174 provided by illumination source 102 at an orientation that is aligned with the x-z plane depicted in FIGS. 7A-C. At this angle, illumination light 172 is oriented perpendicular to the direction of periodicity of the fin structures of structure 170 (i.e., perpendicular to the y-direction).

Values of the parameters of interest (i.e., H, D, TCD, and MCD offset) are estimated based on an analysis of the measurement data associated with measurements of structure 170 at two different azimuth angles with two different characterizations of the dielectric permittivity. FIGS. 8A-8D illustrate the results of these analyses.

Figure 8A:
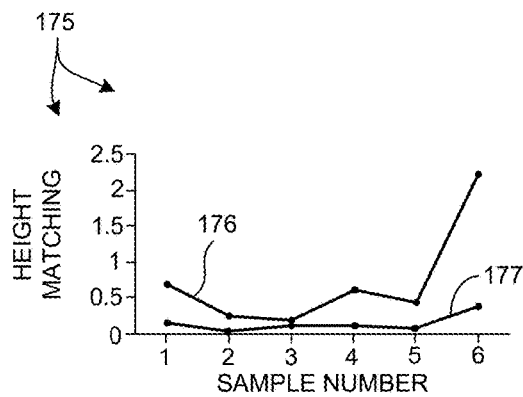
FIGS. 8A-D each depict values of different parameters of interest estimated based on an analysis of measurement data associated with measurements of structure 170 at two different azimuth angles with two different characterizations of the dielectric permittivity.

FIG. 8A depicts a plot 175 of the difference between the values of the height parameter, H, estimated based on an analysis of the measurement data at the first azimuth angle (i.e., parallel to the direction of periodicity) and an analysis of the measurement data at the second azimuth angle (i.e., perpendicular to the direction of periodicity). Plotline 176 illustrates the difference values when an isotropic model of the dielectric permittivity of the materials under measurement is employed. Plotline 177 illustrates the difference values when an anisotropic characterization of the dielectric permittivity of the materials under measurement is employed.

Figure 8B:
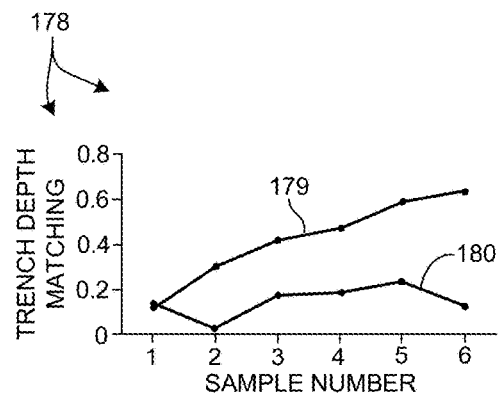

FIG. 8B depicts a plot 178 of the difference between the values of the trench depth parameter, D, estimated based on an analysis of the measurement data at the first azimuth angle and at the second azimuth angle. Plotline 179 illustrates the difference values when an isotropic model of the dielectric permittivity of the materials under measurement is employed. Plotline 180 illustrates the difference values when an anisotropic characterization of the dielectric permittivity of the materials under measurement is employed.

Figure 8C:
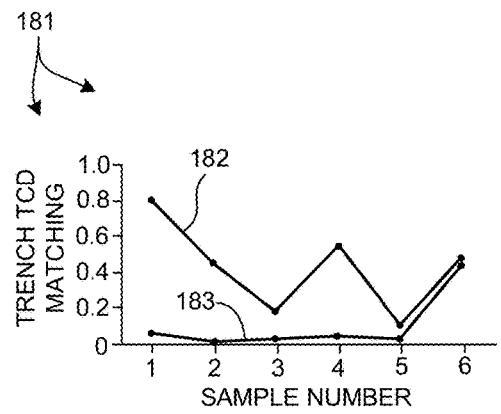

FIG. 8C depicts a plot 181 of the difference between the values of the top CD parameter, TCD, estimated based on an analysis of the measurement data at the first azimuth angle and at the second azimuth angle. Plotline 182 illustrates the difference values when an isotropic model of the dielectric permittivity of the materials under measurement is employed. Plotline 183 illustrates the difference values when an anisotropic characterization of the dielectric permittivity of the materials under measurement is employed.

Figure 8D:
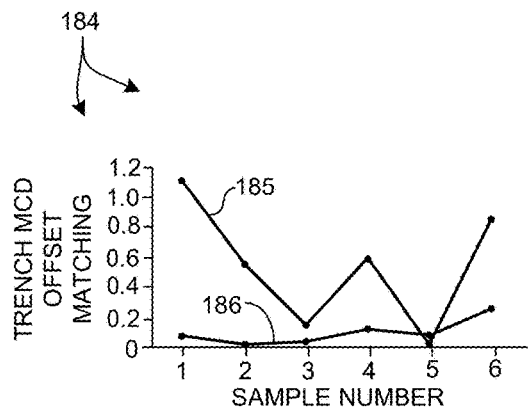

FIG. 8D depicts a plot 184 depicting the difference between the values of the MCD offset parameter (i.e., pitch walk) estimated based on an analysis of the measurement data at the first azimuth angle and at the second azimuth angle. Plotline 185 illustrates the difference values when an isotropic model of the dielectric permittivity of the materials under measurement is employed. Plotline 186 illustrates the difference values when an anisotropic characterization of the dielectric permittivity of the materials under measurement is employed.

As illustrated in FIGS. 8A-8D, when an isotropic model is employed there is poor agreement between the two different measurement subsystems (i.e., the two different azimuth angles). This is understandable because the silicon MCD along the x-direction is very long, but the silicon MCD along the y direction is less than 14 nanometers in this particular example. Since quantum and interface effects are both significant below 20 nanometers, an anisotropic material model may be advantageous. In the measurement examples depicted in plotlines 177, 180, 183, and 186, the dispersion parameters n and k are floated in the analyses of the measurement data associated with both measurement subsystems. As illustrated in FIGS. 8A-8D, when the anisotropic model is employed there is excellent agreement between the two different measurement subsystems.

Figure 9:
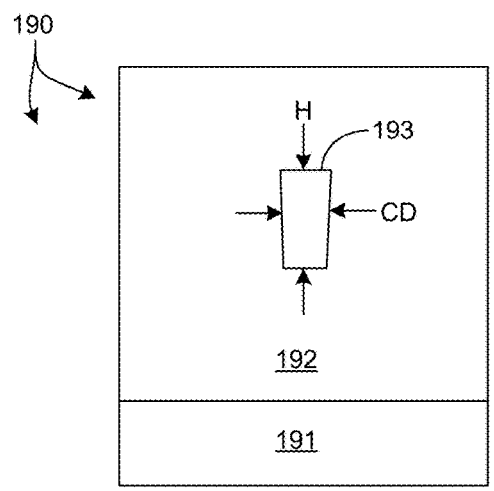
FIG. 9 is a diagram illustrative of an exemplary structure 190 under measurement, for example, by measurement system 100.

FIG. 9 depicts an illustration of an exemplary structure 190 under measurement, for example, by measurement system 100. In this example, structure 190 includes a tungsten grating structure 193 surrounded by silicon dioxide 192 disposed on a silicon substrate 191. The tungsten grating CD is approximately 10 nanometers and the height of the tungsten grating is approximately 30 nanometers.

In this example, the dispersion parameters, n and k, are floated for two different measurement subsystems. The two measurement subsystems are two orthogonal azimuth angles (e.g., Az=0 degrees and Az=90 degrees). Seed values associated with the regression of the dispersion parameter values for both measurement subsystems were set to the measured values of a tungsten film target (e.g., structure 150 depicted in FIG. 3). Regression was performed by fitting analysis module 147 depicted in FIG. 2 to arrive at optimized values for n and k for both measurement subsystems. Without optimization of the dispersion parameters (i.e., isotropic material model), the spectral fitting was extremely poor (i.e., $\chi 2 \sim 15000$). However, after optimization of each of the dispersion parameters associated with each measurement subsystem (i.e., anisotropic material model), the spectral fitting was very good (i.e., $\chi 2 \sim 10$).

Figure 10:
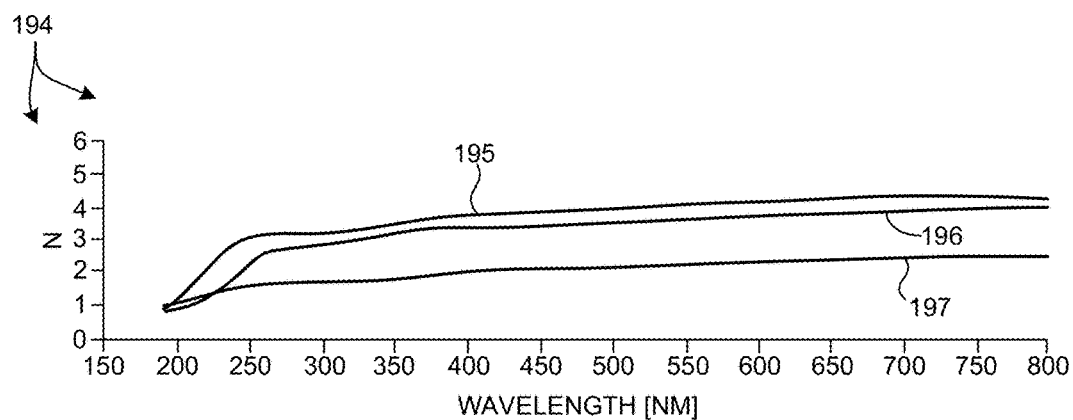
FIG. 10 illustrates a plot of values of the real component, n, of the complex index of refraction measured by measurement system 100 depicted in FIG. 1 over a range of illumination wavelengths.

FIG. 10 depicts a plot 194 of values of the real component, n, of the complex index of refraction measured by measurement system 100 depicted in FIG. 1 over a range of illumination wavelengths. Plotline 197 depicts the measured values of n associated with measurements of a tungsten film target (e.g., structure 150 depicted in FIG. 3). Plotline 196 depicts the measured values of n associated with measurements of the tungsten grating structure 193 (depicted in FIG. 9) at an azimuth angle of zero degrees. Plotline 195 depicts the measured values of n associated with measurements of the tungsten grating structure 193 at an azimuth angle of ninety degrees.

Figure 11:
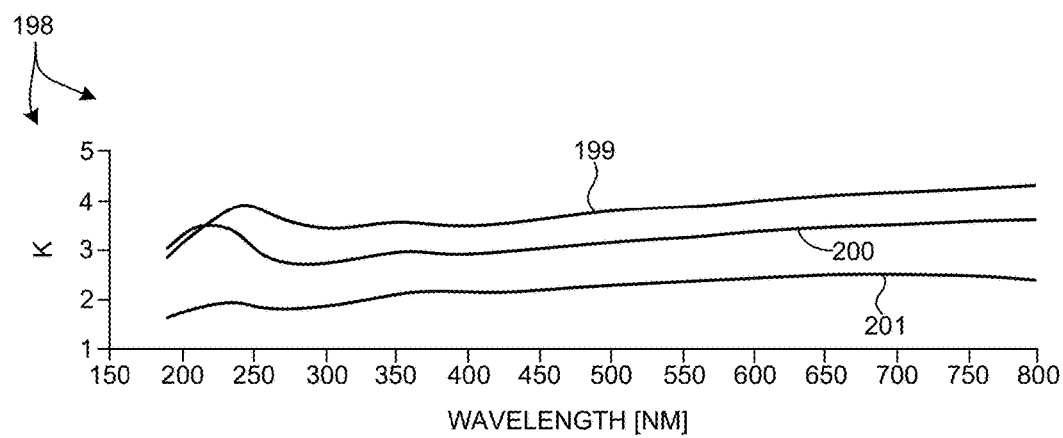
FIG. 11 illustrates a plot of values of the imaginary component, k, of the complex index of refraction measured by measurement system 100 depicted in FIG. 1 over a range of illumination wavelengths.

Similarly, FIG. 11 depicts a plot 198 of values of the imaginary component, k, of the complex index of refraction measured by measurement system 100 depicted in FIG. 1 over a range of illumination wavelengths. Plotline 201 depicts the measured values of n associated with measurements of a tungsten film target (e.g., structure 150 depicted in FIG. 3). Plotline 199 depicts the measured values of n associated with measurements of the tungsten grating structure 193 (depicted in FIG. 9) at an azimuth angle of zero degrees. Plotline 200 depicts the measured values of n associated with measurements of the tungsten grating structure 193 at an azimuth angle of ninety degrees.

As depicted in FIGS. 10 and 11, significant measurement errors are expected if an isotropic characterization of tungsten grating structure 193 is employed.

Figure 12A:
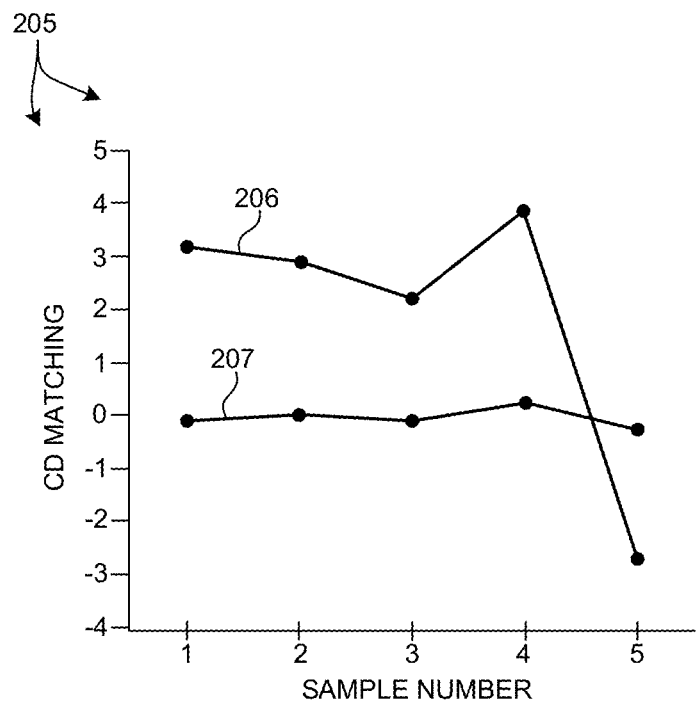
FIG. 12A illustrates a plot of the difference between values of a CD parameter estimated based on an analysis of measurement data at a first azimuth angle and a second azimuth angle for anisotropic and isotropic characterizations of the dielectric permittivity of the materials under measurement.
Figure 12B:
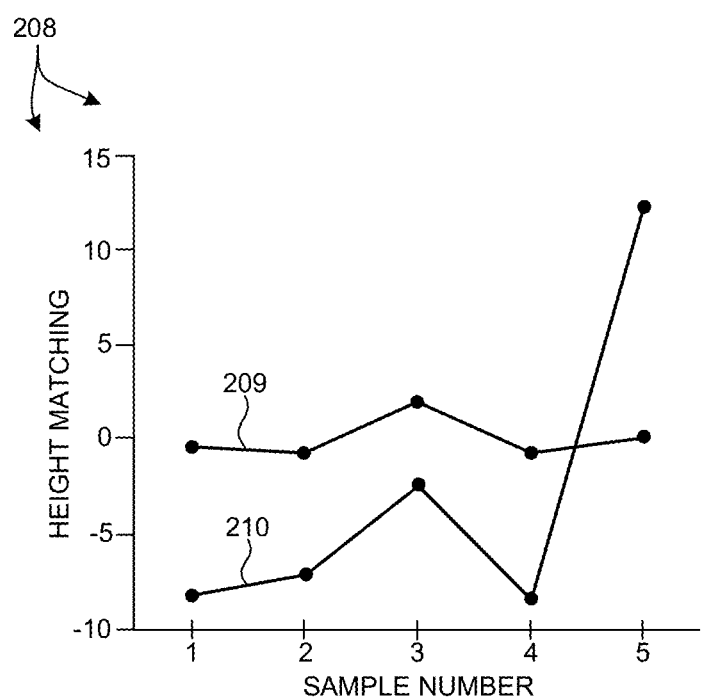
FIG. 12B illustrates a plot of the difference between values of a height parameter estimated based on an analysis of measurement data at a first azimuth angle and a second azimuth angle for anisotropic and isotropic characterizations of the dielectric permittivity of the materials under measurement.

Values of the parameters of interest (i.e., H and CD) are estimated based on an analysis of the measurement data associated with measurements of structure 190 at two different azimuth angles with two different characterizations of the dielectric permittivity. FIGS. 12A-12B illustrate the results of these analyses.

FIG. 12A depicts a plot 205 of the difference between the values of the CD parameter estimated based on an analysis of the measurement data at the first azimuth angle and an analysis of the measurement data at the second azimuth angle. Plotline 206 illustrates the difference values when an isotropic model of the dielectric permittivity of the materials under measurement is employed. Plotline 207 illustrates the difference values when an anisotropic characterization of the dielectric permittivity of the materials under measurement is employed.

FIG. 12B depicts a plot 208 of the difference between the values of the height parameter, H, estimated based on an analysis of the measurement data at the first azimuth angle and at the second azimuth angle. Plotline 210 illustrates the difference values when an isotropic model of the dielectric permittivity of the materials under measurement is employed. Plotline 209 illustrates the difference values when an anisotropic characterization of the dielectric permittivity of the materials under measurement is employed.

As illustrated in FIGS. 12A-12B, when an isotropic model is employed there is poor agreement between the two different measurement subsystems (i.e., the two different azimuth angles). This is understandable because the tungsten CD in one direction is very long, but in the other direction is approximately 10 nanometers. In the measurement examples depicted in plotlines 207 and 209, the dispersion parameters n and k are floated in the analyses of the measurement data associated with both measurement subsystems. As illustrated in FIGS. 8A-8B, when the anisotropic model is employed there is excellent agreement between the two different measurement subsystems.

In the aforementioned examples, the anisotropic material characterization of a structure under measurement is varied depending on changes in the azimuth angle associated with each measurement. However, in general, the anisotropic material characterization of a structure under measurement may be varied depending on changes in any combination of measurement system parameter values.

In another aspect, model based measurements are performed with the assumption that off-diagonal elements of the dielectric permittivity matrix are assumed to be zero valued. This simplifies electromagnetic model building and fitting analysis significantly.

In yet another aspect, model based measurements are performed at azimuth angles selected to align with the principle axes of the geometry under measurement. This assumption may be advantageous when performing measurements of stacked structures having features patterned with periodicity in one direction (e.g., fin structures, gate structures, etc.). In these examples, a measurement is performed in a first direction aligned with the direction of periodicity (e.g., Az=0 degrees) and another measurement is performed in a second direction perpendicular to the first direction (e.g., Az=90 degrees). These simple illumination geometries (Az=0 and Az=90) allow complete de-coupling of p and s polarizations. However, even with polarization de-coupling, more than one refractive index is required to correctly model ellipsometric signals because ellipsometry signals involve both s and p polarizations. In these embodiments, the material characterization of a structure under measurement is varied depending on the azimuth angle associated with each measurement.

In another further aspect, an initial estimate of values of one or more parameters of interest is determined based on optical measurements performed at a single orientation of the incident illumination beam with respect to the measurement target. The initial, estimated values are implemented as the starting values of the parameters of interest for a regression of the measurement model with measurement data collected from optical measurements at multiple orientations. In this manner, a close estimate of a parameter of interest is determined with a relatively small amount of computational effort, and by implementing this close estimate as the starting point for a regression over a much larger data set, a refined estimate of the parameter of interest is obtained with less overall computational effort.

In one example, the initial values of the optical dispersion parameters of each measurement channel (i.e., subsystem) are seeded with bulk parameter values or dispersion parameter values determined from a film target of the same material under measurement.

In another aspect, optical model based measurements of semiconductor structures incorporate a characterization of the optical dispersion of one or more materials comprising the structure under measurement that depends on the geometry of the structure. In some embodiments, the dielectric permittivity of a material comprising a semiconductor structure under measurement is treated as isotropic. In these embodiments, the dielectric permittivity is treated as function of geometry, $\varepsilon(\lambda, g)$. In some other embodiments, the dielectric function is treated as a multidimensional tensor, where one or more of the elements of the multidimensional tensor are treated as functions of geometry, $\varepsilon_{ij}(\lambda, g)$. In some embodiments, the optical dispersion metrics, n and k, depend on the geometric profiles of the structure under measurement in addition to the measurement subsystem parameters (e.g., optical electric field direction, light polarization, AOI, azimuth angle, etc.).

In a further aspect, the optical dispersion parameters are varied during regression as the estimated values of the underlying geometric parameters are iteratively updated. In one example, the floating material parameters are used to monitor the structural parameters of interest using an optical response model that characterizes a quantum effect. In this sense, the estimation of material parameter values characterized in part by geometric parameters enhances measurement sensitivity to the geometric parameters.

Quantum confinement in semiconductor structures causes a change in refractive index and absorption coefficient. This is sometimes referred to as the quantum confinement Stark effect in the presence of a strong, built-in electric field. In this case of semiconductor quantum confinement, the electron-hole wave function overlap increases. This results in an increase in the optical absorption. In addition, a change in refractive index occurs in accordance with the Kramers-Kronig relations. For a semiconductor quantum well under a built-in electric field, the electron-hole wave-function overlap decreases resulting in a decrease in optical absorption and a concomitant change in the index of refraction. In these cases, the assumption of an isotropic optical material response leads to measurement errors.

A quantum effect occurs in quantum well structures, quantum wire structures, quantum dot structures, etc., of some materials (e.g., metals and semiconductors). A quantum well may be defined as a layer capable of confining particles, such as electrons and holes, in the dimension perpendicular to the layer surface or interface. Movement in the two, orthogonal directions remains unrestricted. Hence, a quantum well is a one-dimensional confining system.

A quantum well can be made by joining different materials together. Physically, a quantum well is a thin layer surrounded by two other layers with wider bandgaps. The thin layer is commonly referred to as a "well" and the surrounding layers on each side of the "well" are each referred to as a "barrier". Typically, a quantum confinement effect arises in semiconductor materials when the thickness of the well structure (e.g., layer) is less than 20 nanometers. For metals, a quantum confinement effect may arise at larger thicknesses.

Figure 13:
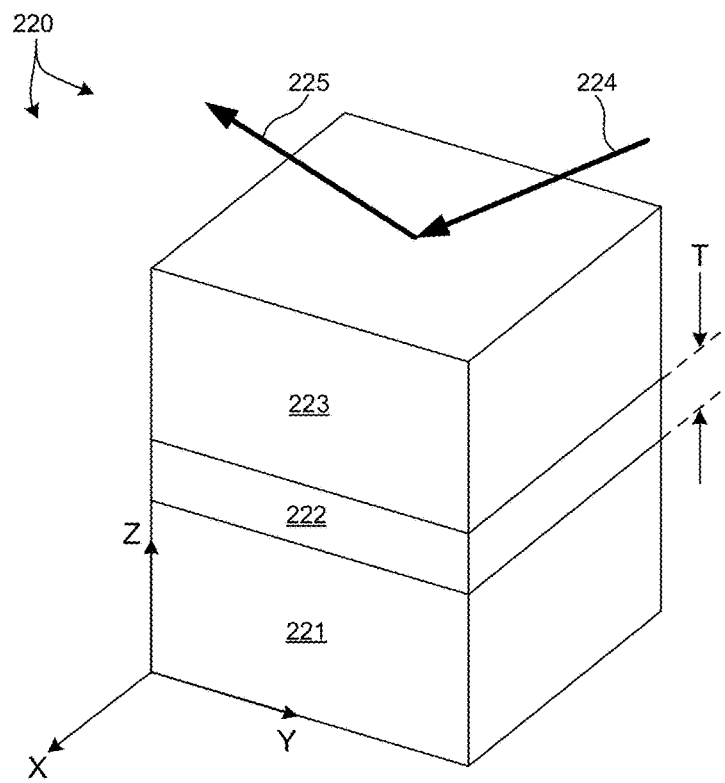
FIG. 13 is a diagram illustrative of an exemplary structure 220 under measurement, for example, by measurement system 100.

FIG. 13 depicts an exemplary structure 220 under measurement, for example, by measurement system 100. In this example, a thin layer 222 of Tungsten having a thickness, T, is sandwiched between layers 221 and 223 of materials different from Tungsten. In some examples, the thickness of the Tungsten layer is less than 20 nanometers. Light 225 is collected by spectrometer 104 in response to illumination light 224 provided by illumination source 102. Semiconductor film stack structure 220 is fabricated as a quantum well. Layer 222 is a thin layer of material (i.e., the well) sandwiched between layers 221 and 223 (i.e., the barriers). Fabrication technologies such as Metal Beam Epitaxy (MBE) and Metal-Organic Chemical Vapor Deposition (MOCVD) are employed to fabricate thin layers, such as layers 221-223. Layers 221-223 are relatively thin in the z-direction, having dimensions in the x and y directions that are relatively large.

In this example, quantum confinement occurs in the z-direction. As described hereinbefore, the material-optical response properties associated layer 222 are anisotropic. The dielectric permittivity of the well layer along the z-direction is different from the dielectric permittivity in the x and y directions. However, the optical response itself is independent of the illumination azimuth angle.

Figure 14:
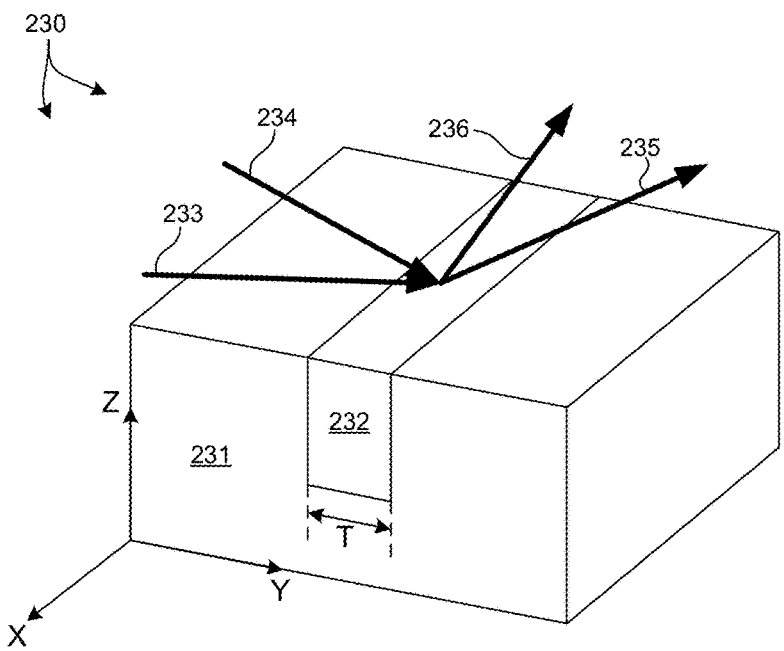
FIG. 14 is diagram illustrative of an exemplary structure 230 under measurement, for example, by measurement system 100.

FIG. 14 depicts an exemplary structure 230 under measurement, for example, by measurement system 100. In this example, a thin layer 232 of Tungsten having a thickness, T, is surrounded by a different material 231. In some examples, the thickness of the Tungsten layer 232 is less than 20 nanometers. In one measurement, light 235 is collected by spectrometer 104 in response to illumination light 233 provided by illumination source 102. In another measurement, light 236 is collected by spectrometer 104 in response to illumination light 234 provided by illumination source 102.

Advanced lithography techniques, including multiple patterning techniques, enable the fabrication of lateral (CD) structures with a thickness of less than 20 nanometers. During the semiconductor fabrication process flow, quantum wells in the x-y plane such as structure 220 depicted in FIG. 13 are purposely fabricated by MBE and MOCVD. However, "vertical" quantum wells, such as structure 230, are unintentionally fabricated as a result of shrinking device dimensions. These unintentional, "vertical" quantum well structures do not significantly impact device performance or yield, but they do have a significant impact on spectroscopic measurement results. In this example, the dielectric permittivity of the well layer along the y-direction is different from the dielectric permittivity in the x-direction. As a result, the optical response is dependent on the illumination azimuth angle.

The most commonly used dispersion model is the Lorentz model, a.k.a., the harmonic oscillator model. The Lorentz model treats the oscillations of electrons bound to atoms in a material under optical illumination as an ensemble of harmonic oscillators. In one example, the representation of the dielectric function is described in equation (6), $$\varepsilon(E) = n_b + \frac{\sum_{s=1}^{m} H_s(E)}{1 - \sum_{s=1}^{m} v_s H_s(E)} \quad (6)$$

where $n_b$ is the uniform background index (default value=1), E is the electric field energy expressed as a function of the wavelength, $\lambda$, by E=1,240/$\lambda$, $H_s$ is the contribution of the sth oscillator, and $v_s$ is the local field correction factor for the sth oscillator. $v_s$ is equal to zero for metals, close to zero for most semiconductors, and equal to 0.333 for ideal dielectrics. $H_s$ is described in further detail be equation (7), $$H_s = \frac{16\pi N_s R_y^2 r_0^3}{(E_{ns}^2 - E^2 + iE_{gs}E)} e^{-i\Phi_s} \quad (7)$$

where, $R_y$ is the Rydberg constant (equal to 13.6058 eV), $r_0$ is the Bohr radius (equal to 0.0529177 nanometers), $N_s$ is the number density of the sth oscillator which represents the relative importance of this oscillator, $E_{ns}$ is the resonance energy of the sth oscillator, $E_{gs}$ is the damping constant energy of the sth oscillator, and $\Phi_s$ is the relative phase of the sth oscillator. The lowest valued resonance energy is often called the bandgap energy. The Lorentz model is commonly used to describe most materials specifically those with several peaks including semiconductors materials, such as Si, Ge, SiGe, and metals, such as W, Cu, Co, etc.

The oscillator parameters in equation (7) are sensitive to the quantum confinement effect in the direction of confinement (e.g., the z-direction in FIG. 13 and the y-direction in FIG. 14).

The resonance energy $E_{ns}$ and the oscillator strength $N_s$ are the most sensitive. In addition, a model of a structure exhibiting quantum confinement should include a larger number of oscillators due to the discretization of energy levels.

Schrödinger's equation in one dimension (i.e., the direction of confinement) explains the basic properties of a quantum well as illustrated in equation (8), $$\frac{-\hbar^2}{2m} \frac{d^2\psi_n}{dz^2} + V(z)\psi_n = E_n\psi_n \quad (8)$$

where V(z) is the quantum well potential seen by the particle along the direction of confinement (z direction in this example) and $\psi_n$ is the wavefunction. Where the well is considered infinitely high at each side, the solution of equation (8) is given by equations (9) and (10), $$E_n = \frac{-\hbar^2}{2m}\left[\frac{n\pi}{L_z}\right]^2 \quad n = 1, 2, \ldots \quad (9)$$

$$\psi_n = A\sin\left(\frac{n\pi z}{L_z}\right) \quad n = 1, 2, \ldots \quad (10)$$

where $L_z$ is the dimension of the well in the z-direction and z is the location within the well in the z-direction.

Combining equation (9) with equation (7) makes it clear that the energy levels of each oscillator ($E_{ns}$) are dependent of the well dimensions in the direction of confinement when quantum confinement effects are accounted for in the measurement model.

For Silicon, Germanium and Cadmium Selenide nanocrystals the relationship between the bandgap at room temperature and the size of the structure, d, is approximated by equation (11), $$E_{bandgap}(d) = E_{bandgap0} + \beta/d^\alpha \quad (11)$$

where $E_{bandgap0}$ is the bulk bandgap, and $\beta$ and $\alpha$ depend on the material as well as the size of the nanostructure (i.e., quantum well thickness). For silicon nanostructures, equation (11) is approximated by equation (12).

$$E_{bandgap}(d) = E_{bandgap0} + 3.73/d^{1.73} \quad (12)$$

For a silicon nanostructure, equation (12) is substituted into equations (6) and (7) to represent the dielectric permittivity as a function of dimensions of the structure under measurement.

In general, several methodologies can be used to incorporate dependence of dielectric functions on the geometry and size of the feature within the scope of this patent document. In one example, Maxwell-Garnett effective medium theory is employed to model the dependence of dielectric functions on the geometry and size of the feature under measurement.

In some examples, the optical dispersion parameters, n and k, are parametrized such that they are dependent on the geometric parameters of the structure, e.g., $n_j$ ($\lambda$; CD, HT, SWA) and $k_j$ ($\lambda$; CD, HT, SWA).

In one example, equation (13) expresses the optical absorption coefficient of a silicon nanostructure as a function of the bandgap based on the relationship between bandgap and quantum well thickness illustrated in equation (12).

$$\alpha(\omega,d) = 2.77e6[(E/E_{bandgap})(E_{bandgap}+0.044)/(3E_{bandgap}+0.088)](\hbar\omega - E{bandgap})^{0.5} \quad (13)$$

Similarly, equation (14) expresses the imaginary part of the dielectric function as a function of the bandgap based on the relationship between bandgap and quantum well thickness illustrated in equation (12).

$$\varepsilon_2(\omega,d) = 92(E_{bandgap}/\hbar\omega)E_{bandgap}+0.044)/(3E_{bandgap}+0.088)](\hbar\omega - Eg)^{0.5}/\hbar\omega \quad (14)$$

The parametrization of the optical parameters may be implemented based on one of the effective medium theory approximations, or in another way. Effective medium theory or other theories may be used to account for the behavior of dielectric functions in the quantum regime. In one example, a linear transition is assumed between tabulated bulk behavior and behavior at geometries known to express quantum effects. Look up tables with interpolation between bulk and quantum behavior may also be used.

Figure 15:
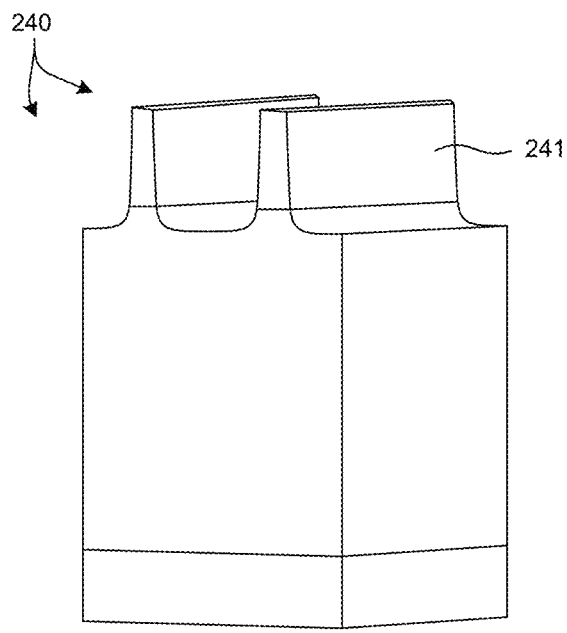
FIG. 15 is a diagram of an exemplary structure 240 under measurement, for example, by measurement system 100. In this example, a silicon fin structure 241 having a critical dimension of less than 20 nanometers is measured.

FIG. 15 depicts an exemplary structure 240 under measurement, for example, by measurement system 100. In this example, a silicon fin structure 241 having a critical dimension of less than 20 nanometers is measured.

In this example, a number of different fin structures are measured each having a different known CD values. A Lorentz model including five harmonic oscillators is implemented in accordance with equations (5) and (6). In addition, the bandgap energy is related to the geometry of the structure 241 in accordance with equation (12). Bulk silicon dispersion parameter values were used as the seed values for the dispersion parameters. A regression analysis of the measurement model was performed based on the measurement data to optimize the values of the dispersion parameters.

Figure 16:
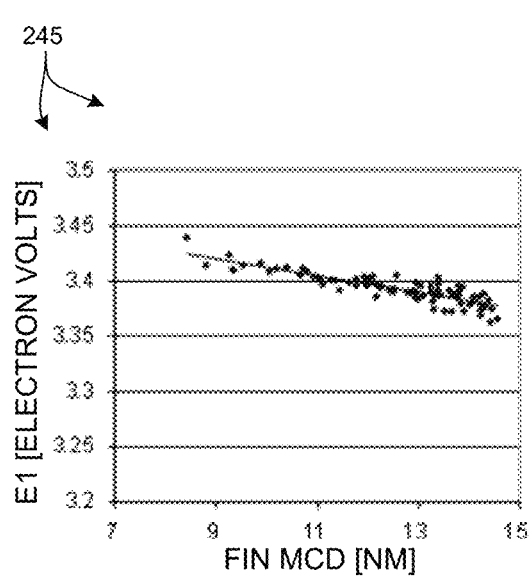
FIG. 16 illustrates a plot 245 of the values of the resonance energy, E1, associated with the first oscillator of the Lorentz model for different CD values of a fin structure.
Figure 17:
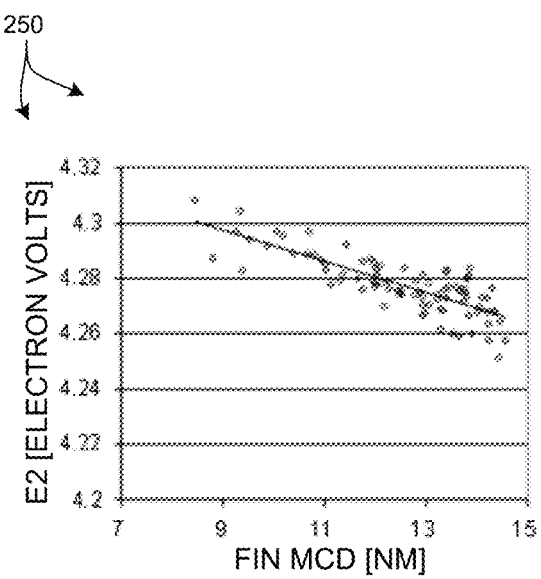
FIG. 17 illustrates a plot 250 of the values of the resonance energy, E2, associated with the second oscillator of the Lorentz model for different CD values of fin structure 241.

FIG. 16 illustrates a plot 245 depicting the values of the resonance energy, E1, associated with the first oscillator of the Lorentz model for different CD values of fin structure 241. FIG. 17 illustrates a plot 250 depicting the values of the resonance energy, E2, associated with the second oscillator of the Lorentz model for different CD values of fin structure 241. As illustrated in FIGS. 16 and 17, both E1 and E2 vary in accordance with the quantum effect, which predicts that the energy level increases as the well narrows.

In a further aspect, one or more of the elements of the multidimensional tensor describing the dielectric permittivity are modelled differently. For example, different multi-oscillator models may be used for different elements of the multidimensional tensor, $\varepsilon_{ij}(\lambda,g)$. The oscillator constants associated with each different model of the model depend on the structure geometry. In these examples, an element of a multidimensional tensor describing the dielectric permittivity of the materials comprising the structure is modelled differently from another element of the multidimensional tensor.

In some embodiments, a geometric parameter of interest (e.g., H, CD, depth, etc.) is estimated based on a difference between the dispersion parameter values estimated based on an isotropic model and the same dispersion parameter values estimated based on an anisotropic model of optical dispersion. In one example, computing system 116 of measurement system 100 depicted in FIG. 1 estimates a value of the thickness, T, of feature 157 based on the difference between the estimated n and k values depicted in FIGS. 5 and 6, respectively.

As depicted in FIG. 1, measurement system 100 is a spectroscopic ellipsometer. However, in general, measurement system 100 may be configured as a spectroscopic ellipsometer, a spectroscopic reflectometer, a rotating polarizer, rotating compensator spectroscopic ellipsometer (RPRC SE), a polarizing spectroscopic reflectometer, a photo reflectometer, etc. In general, the techniques described herein may be applied to measurement data collected from any model based spectroscopic measurement system, or combination of model based spectroscopic measurement systems.

In a further aspect, a measurement recipe (i.e., combinations of different measurement system parameters, different measurement systems, or both) associated with a particular measurement application is optimized for highest sensitivity and lowest correlation among floating parameters of the anisotropic model of optical dispersion.

Figure 18:
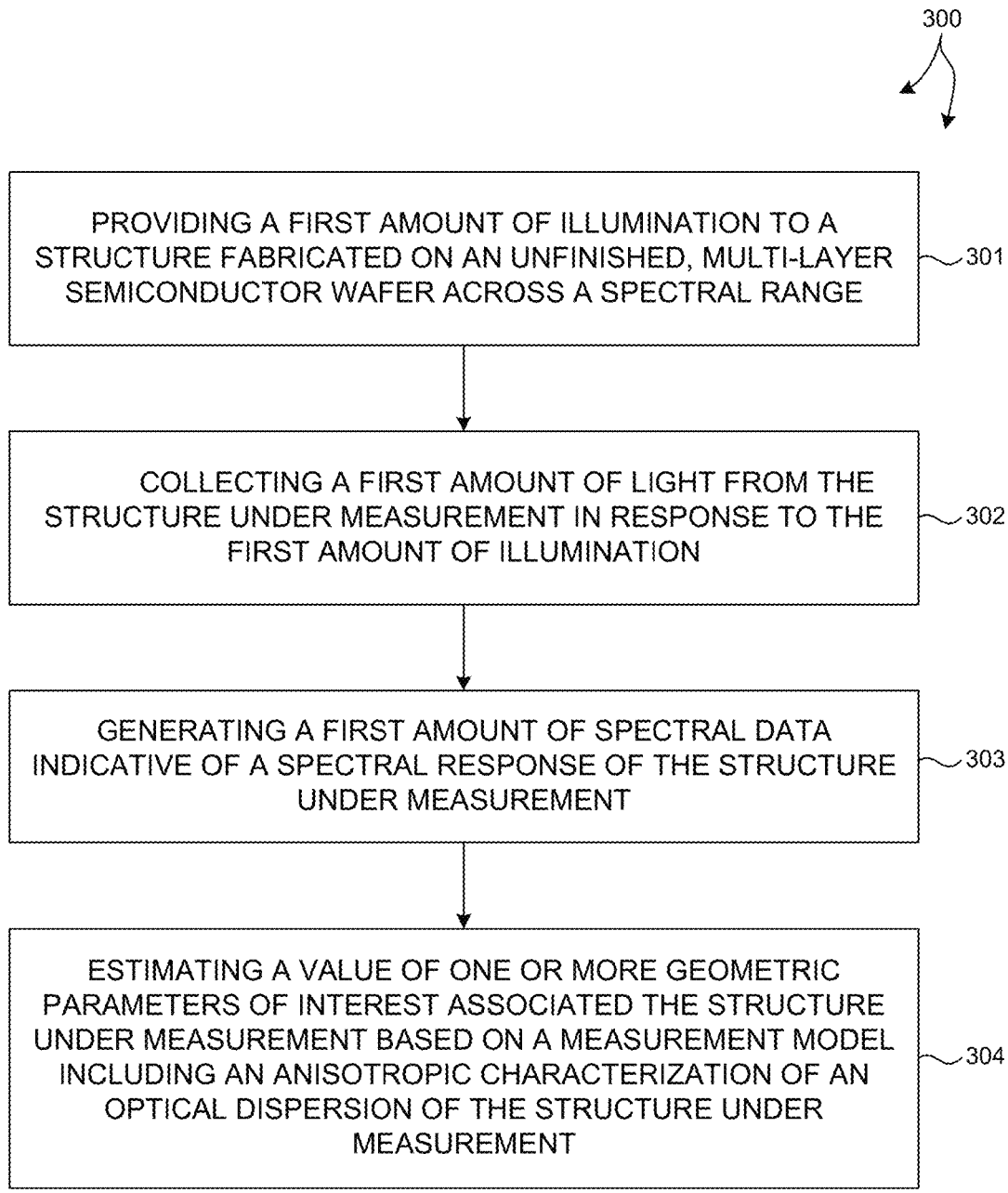
FIG. 18 illustrates a process flow 300 suitable for implementation by the system 100 of the present invention in at least one novel aspect.

FIG. 18 illustrates a process flow 300 suitable for implementation by the system 100 of the present invention. In one aspect, it is recognized that data processing steps of the process flow 300 may be carried out via a pre-programmed algorithm executed by one or more processors of computing system 116. While the following description is presented in the context of system 100, it is recognized herein that the particular structural aspects of system 100 do not represent limitations and should be interpreted as illustrative only.

In block 301, a first amount of illumination is provided to a structure fabricated on an unfinished, multi-layer semiconductor wafer across a spectral range, for example, by illuminator 102.

In block 302, a first amount of light is collected from the structure under measurement in response to the first amount of illumination, for example, by spectrometer 104.

In block 303, a first amount of spectral data indicative of a spectral response of the structure under measurement is generated, for example, by spectrometer 104.

In block 304, a value of one or more geometric parameters of interest associated with the structure under measurement is estimated, for example, by computing system 116, based on a measurement model including an anisotropic characterization of an optical dispersion of the structure under measurement.

In another further aspect, device performance is improved by controlling a process of manufacture of the semiconductor wafer based at least in part on the estimated parameters of interest. In one example, CD may be controlled based on CD values estimated based on an anisotropic characterization of optical dispersion as described herein.

In another further aspect, separate estimates of parameters of interest associated with different features of a structure under measurement are made based on the same spectral response data. For example, a wafer under measurement may include multiple layers and structural features. The spectral response data received from spectrometer 104 includes contributions from all of these layers and features. A measurement model that captures the contributions of each of these layers and features can be used to separately determine parameters of interest associated with each different physical layer or feature under analysis.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

As used herein, the term "wafer" generally refers to substrates formed of a semiconductor or non-semiconductor material. Examples of such a semiconductor or non-semiconductor material include, but are not limited to, monocrystalline silicon, silicon on insulator, strained silicon on insulator, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

A typical semiconductor process includes wafer processing by lot. As used herein a "lot" is a group of wafers (e.g., group of 25 wafers) which are processed together. Each wafer in the lot is comprised of many exposure fields from the lithography processing tools (e.g. steppers, scanners, etc.). Within each field may exist multiple die. A die is the functional unit which eventually becomes a single chip. One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, it is to be understood that the embodiments may be used for characterizing structures of another specimen such as a reticle, which may also be commonly referred to as a mask or a photomask. Many different types of reticles are known in the art, and the terms "reticle," "mask," and "photomask" as used herein are intended to encompass all types of reticles known in the art.

Although embodiments are described herein with respect to measurement of structures applied to wafers, it is to be understood that the methods and systems disclosed herein may be used for characterizing critical dimensions of semiconductor structures, overlay among layers of semiconductor structures, and material composition of semiconductor structures.

The embodiments described herein generally relate to methods for determining parameters of interest of multi-layer structures based on optical model parameter values at high throughput. For example, one embodiment relates to a computer-implemented method for determining critical dimensions of multi-layer structures based on optical model parameter values derived from spectroscopic ellipsometer data. However, in other examples, measurement of critical dimensions, overlay, and material composition using the techniques described herein is also contemplated. Similarly, the methods described herein are not limited in the types of metrology systems from which optical model parameter values may be derived. For example, in one embodiment, the metrology system includes a reflectometer. In general, the optical dispersion models described herein may be applied to the analysis of measurement data received from a variety of broadband and narrowband metrology tools. For example, spectroscopic ellipsometers and reflectometers, multi-angle ellipsometers and reflectometers, including any number or type of illumination sources (e.g., lamp or laser based sources emitting light in the visible, infra-red, ultra-violet, vacuum ultraviolet, deep ultraviolet spectrums) may be contemplated within the scope of this patent document.

In addition, the metrology system may be configured for inspection of patterned wafers and/or unpatterned wafers. The inspection system may be configured as a LED inspection tool, edge inspection tool, backside inspection tool, macro-inspection tool, or multi-mode inspection tool (involving data from one or more platforms simultaneously), and any other metrology or inspection tool that benefits from the determination of structural characteristics of multi-layer structures based on optical model parameter values at high throughput. Thus, the terms "metrology" system and "inspection" system may be used interchangeably.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A measurement system comprising:
a first illuminator providing a first amount of illumination to a structure fabricated on an unfinished, multi-layer semiconductor wafer across a spectral range;
a first spectrometer collecting a first amount of light from the structure under measurement in response to the first amount of illumination and generating a first amount of spectral data indicative of a spectral response of the structure under measurement, wherein the first illuminator and the first spectrometer are configured in accordance with a first set of measurement system parameters; and
a fitting analysis module configured to estimate a value of one or more geometric parameters of interest associated with the structure under measurement based on a measurement model including an anisotropic model of an optical dispersion of the structure under measurement, the anisotropic model comprising a multidimensional tensor characterizing a dielectric permittivity of the structure, the multidimensional tensor having a plurality of scalar components, wherein a value of at least one of the plurality of scalar components is different from a value of another of the plurality of scalar components of the multidimensional tensor.

2. The measurement system of claim 1, wherein the structure under measurement includes two or more geometric features each fabricated from a different material, and wherein the measurement model includes a different anisotropic model of the optical dispersion associated with each different material.

3. The measurement system of claim 1, wherein the estimating of the value of the one or more geometric parameters of interest involves a regression of the first amount of spectral data with the measurement model.

4. The measurement system of claim 1, wherein the first illuminator and the first spectrometer are configured as a spectroscopic ellipsometer or a spectroscopic reflectometer.

5. The measurement system of claim 1, wherein the anisotropic model of the optical dispersion of the structure under measurement includes a matrix function of the optical dispersion.

6. The measurement system of claim 5, wherein each of the off-diagonal elements of the matrix function are zero valued, and two or more of the diagonal elements of the matrix function are different values.

7. The measurement system of claim 1, wherein the anisotropic model of the optical dispersion includes one or more optical dispersion parameters associated with each of three principle directions, and wherein the one or more optical dispersion parameter values associated with at least one of the three principle directions is different from the one or more optical dispersion parameter values associated with the other of the three principle directions.

8. The measurement system of claim 1, further comprising:
a second illuminator providing a second amount of illumination to the structure under measurement; and
a second spectrometer collecting a second amount of light from the structure under measurement in response to the second amount of illumination and generating a second amount of spectral data indicative of a spectral response of the structure under measurement, wherein the second illuminator and the second spectrometer are configured in accordance with a second set of measurement system parameters.

9. The measurement system of claim 8, wherein the first and second illuminators are the same illuminator and the first and second spectrometers are the same spectrometer.

10. The measurement system of claim 8, wherein the first set of measurement system parameters includes an azimuth angle, an angle of incidence, an illumination light polarization, an optical electric field orientation, or any combination thereof, and wherein the second set of measurement system parameters includes a different value of any of the azimuth angle, the angle of incidence, the illumination light polarization, and the optical electric field orientation.

11. The measurement system of claim 8, wherein the estimating of the value of the one or more geometric parameters of interest involves a regression of the first and second amounts of spectral data with the measurement model, wherein one or more optical dispersion parameters associated with a material of the structure under measurement are floated during the regressions of the first and second amounts of spectral data and the values of the one or more geometric parameters of interest are constrained to be the same value during the regressions of the first and second amounts of spectral data.

12. The measurement system of claim 11, wherein an initial value of the one or more optical dispersion parameters employed during the regression of the first and second amounts of spectral data is a bulk, isotropic value of the one or more optical dispersion parameters.

13. The measurement system of claim 12, wherein the bulk, isotropic value of the one or more optical dispersion parameters is determined from a spectroscopic measurement of a film of the material.

14. The measurement system of claim 1, wherein one or more of the plurality of scalar components of the multidimensional tensor is a function of a geometric parameter of the structure under measurement.

15. The measurement system of claim 14, wherein the geometric parameter is one of the geometric parameters of interest.

16. The measurement system of claim 14, wherein one or more of the plurality of scalar components of the multidimensional tensor includes a plurality of harmonic oscillator functions.

17. A method comprising:
providing a first amount of illumination to a structure fabricated on an unfinished, multi-layer semiconductor wafer across a spectral range;
collecting a first amount of light from the structure under measurement in response to the first amount of illumination;
generating a first amount of spectral data indicative of a spectral response of the structure under measurement; and
estimating a value of one or more geometric parameters of interest associated with the structure under measurement based on a measurement model including an anisotropic model of an optical dispersion of the structure under measurement, the anisotropic model comprising a multidimensional tensor characterizing a dielectric permittivity of the structure, the multidimensional tensor having a plurality of scalar components, wherein a value of at least one of the plurality of scalar components is different from a value of another of the plurality of scalar components of the multidimensional tensor.

18. The method of claim 17, wherein the structure under measurement includes two or more geometric features each fabricated from a different material, and wherein the measurement model includes a different anisotropic model of the optical dispersion associated with each different material.

19. The method of claim 17, wherein the anisotropic model of the optical dispersion of the structure under measurement includes a matrix function of the optical dispersion.

20. The method of claim 17, wherein the anisotropic model of the optical dispersion includes one or more optical dispersion parameters associated with each of three principle directions, and wherein the one or more optical dispersion parameter values associated with at least one of the three principle directions is different from the one or more optical dispersion parameter values associated with the other of the three principle directions.

21. The method of claim 17, wherein the anisotropic model of the optical dispersion of the structure under measurement is a function of a geometric parameter of the structure under measurement.

22. The method of claim 21, wherein the geometric parameter is one of the geometric parameters of interest.

23. A measurement system comprising:
a first illuminator providing a first amount of illumination to a structure fabricated on an unfinished, multi-layer semiconductor wafer across a spectral range;
a first spectrometer collecting a first amount of light from the structure under measurement in response to the first amount of illumination and generating a first amount of spectral data indicative of a spectral response of the structure under measurement, wherein the first illuminator and the first spectrometer are configured in accordance with a first set of measurement system parameters; and
a non-transitory, computer readable medium storing instructions that, when executed by one or more processors, cause the one or more processors to:
estimate a value of one or more geometric parameters of interest associated with the structure under measurement based on a measurement model including an anisotropic model of an optical dispersion of the structure under measurement, the anisotropic model comprising a multidimensional tensor characterizing a dielectric permittivity of the structure, the multidimensional tensor having a plurality of scalar components, wherein a value of at least one of the plurality of scalar components is different from a value of another of the plurality of scalar components of the multidimensional tensor.

24. The measurement system of claim 23, wherein the structure under measurement includes two or more geometric features each fabricated from a different material, and wherein the measurement model includes a different anisotropic model of the optical dispersion associated with each different material.

25. The measurement system of claim 23, wherein the anisotropic model of the optical dispersion of the structure under measurement includes a matrix function of the optical dispersion.

26. The measurement system of claim 23, wherein the anisotropic model of the optical dispersion includes one or more optical dispersion parameters associated with each of three principle directions, and wherein the one or more optical dispersion parameter values associated with at least one of the three principle directions is different from the one or more optical dispersion parameter values associated with the other of the three principle directions.

27. The measurement system of claim 23, wherein the anisotropic model of the optical dispersion of the structure under measurement is a function of a geometric parameter of the structure under measurement.

* * * * *